(12) United States Patent
Antz et al.

(10) Patent No.: US 12,714,605 B2
(45) Date of Patent: Aug. 25, 2026

(54) SYSTEMS AND METHODS OF TYMPANOSTOMY TUBE DELIVERY

(71) Applicants: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

(72) Inventors: Andrew G. Antz, Redwood City, CA (US); Matthew D. Mertz, Los Altos, CA (US); Rohit K. Girotra, San Francisco, CA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 421 days.

(21) Appl. No.: 18/247,153

(22) PCT Filed: Oct. 6, 2021

(86) PCT No.: PCT/US2021/053769
§ 371 (c)(1),
(2) Date: Mar. 29, 2023

(87) PCT Pub. No.: WO2022/093504
PCT Pub. Date: May 5, 2022

(65) Prior Publication Data

US 2023/0372156 A1 Nov. 23, 2023

Related U.S. Application Data

(60) Provisional application No. 63/106,553, filed on Oct. 28, 2020.

(51) Int. Cl.
*A61F 11/20* (2022.01)

(52) U.S. Cl.
CPC .................................. *A61F 11/202* (2022.01)

(58) Field of Classification Search
CPC .................. A61F 11/202; A61F 11/20; A61B 2017/00787
(Continued)

(56) References Cited

U.S. PATENT DOCUMENTS 5,497,863 A * 3/1996 Schmidt .................... F16F 9/12 188/306
2009/0299379 A1 12/2009 Katz et al.
(Continued)

FOREIGN PATENT DOCUMENTS

WO WO-2010083308 A1 * 7/2010 ........... A61N 1/0551
WO 2011008948 A1 1/2011

OTHER PUBLICATIONS

International Search Report and Written Opinion for International Application No. PCT/US2021/053769, International Filing Date Oct. 6, 2021, Date of Mailing Jan. 25, 2022.

*Primary Examiner* — Katherine H Schwiker
*Assistant Examiner* — Zehra Jaffri
(74) *Attorney, Agent, or Firm* — Dickinson Wright PLLC; Mark E. Scott

(57) ABSTRACT

Tube delivery. One example is a tube delivery system comprising: a hand piece body; a shaft assembly extending from the hand piece body; and a drive assembly. The shaft assembly may comprise: an elongate outer tube; an introducer (310) defining a distal end, a first leaf on the distal end, a second leaf on the distal end, and an inside diameter; a tympanostomy tube disposed within and abutting the inside diameter of the introducer; and a pusher concentrically disposed within the introducer. The drive assembly may be
(Continued)

disposed within the hand piece body, the drive assembly configured to longitudinally translate the introducer and the pusher relative to the elongate outer tube, wherein the drive assembly is configured to dilate the first leaf (508) and second leaf (510) by the pusher distally translating the tympanostomy tube relative to the introducer.

13 Claims, 17 Drawing Sheets

(58) Field of Classification Search
USPC .......................................................... 606/109
See application file for complete search history.

(56) References Cited

U.S. PATENT DOCUMENTS

| | | | | |
|---|---|---|---|---|
| 2014/0277050 | A1* | 9/2014 | Andreas | A61F 11/202<br>606/185 |
| 2016/0038342 | A1 | 2/2016 | Van et al. | |
| 2016/0045371 | A1* | 2/2016 | Girotra | A61F 11/202<br>606/109 |

* cited by examiner 110
102
100
108
118
120
122
113
112
104
114
116
117
124
O 100
202
118
120
122
ODS
ODT
104
124
200
116

SYSTEMS AND METHODS OF TYMPANOSTOMY TUBE DELIVERY

CROSS-REFERENCE TO RELATED APPLICATIONS

This application is a U.S. National Phase of entry of PCT Application No. PCT/US2021/053769 filed Oct. 6, 2021 titled "Systems and Methods of Tympanostomy Tube Delivery." The PCT application claims the benefit of U.S. Provisional App. No. 63/106,553 filed Oct. 28, 2020 and titled "Systems and Methods of Tube Delivery." Both the PCT and the provisional application are incorporated by reference herein as if reproduced in full below.

BACKGROUND

Otologic procedures involve the insertion of a medical instrument into an ear of a patient, and in some cases use a surgical microscope that requires a line-of-sight view to a target treatment area. When operating with an instrument within the ear canal, the access path of the instrument oftentimes overlaps or blocks the line of sight between the microscope and the target treatment area.

Moreover, any mechanical sound created by the medical instrument may be conveyed directly to the tympanic membrane, and thus the mechanical sound will be perceived as a loud noise or sound by the patient. While adults may understand the situation, young children (e.g., children undergoing bilateral tympanostomy procedure) may be uncooperative for the procedure in the second ear if loud sounds are perceived in the first ear.

Thus, any new design or feature which increases the visibility into the ear, decreases the noise produced during the procedure, reduces the cost of the procedure, and/or reduces the cost of the instruments used in the procedure, would provide a competitive advantage in the marketplace.

SUMMARY

One example is a tube delivery system comprising: a hand piece; a shaft assembly extending distally from the hand piece, and a drive assembly disposed within the hand piece. The shaft assembly may comprise: an elongate outer tube; an introducer defining a distal end, a first leaf on the distal end, a second leaf on the distal end, and an inside diameter, the introducer concentrically disposed within the elongate outer tube; a tympanostomy tube disposed within and abutting the inside diameter of the introducer; and a pusher concentrically disposed within the introducer. The drive assembly the drive assembly is configured to longitudinally translate the introducer and the pusher relative to the elongate outer tube, wherein the drive assembly is configured to dilate the first leaf and the second leaf by the pusher distally translating the tympanostomy tube relative to the introducer.

In the example tube delivery system, the introducer may further comprise: a first longitudinal kerf on a first side of the introducer between the first leaf and the second leaf; and a second longitudinal kerf, the second longitudinal kerf on a second side between the first leaf and the second leaf. In some cases, the first longitudinal kerf and the second longitudinal kerf are co-planar with a longitudinal central axis of the introducer.

The example tube delivery system may further comprise: a first longitudinal kerf on a first side of the introducer between the first leaf and the second leaf; a first circumferential kerf that intersects a proximal end of the first longitudinal kerf; a second longitudinal kerf on a second side of the introducer between the first leaf and the second leaf; and a second circumferential kerf that intersects a proximal end of the second longitudinal kerf. In some cases, the first circumferential kerf and the second circumferential kerf are coplanar, and a plane defined by the first and second circumferential kerfs is perpendicular to a longitudinal central axis of the introducer at the distal end of the introducer. The example tube delivery system may further comprise: a first strain relief aperture at a first end of the first circumferential kerf; a second strain relief aperture at a second end of the first circumferential kerf; a third strain relief aperture at a first end of the second circumferential kerf; and a fourth second strain relief aperture at a second end of the second circumferential kerf.

In the example tube delivery system, the shaft assembly may further comprise: a proximal portion defining a proximal longitudinal axis; a distal portion defining a distal longitudinal axis; and a bend between the proximal portion and the distal portion; wherein an obtuse angle between the proximal longitudinal axis and the distal longitudinal axis is between and including 170 angular degrees and 160 angular degrees. The example shaft assembly may further comprise: the distal portion define a distal length; the bend defines an arc length; and wherein a ratio of the distal length to the arc length is 0.8 or less. In some cases, an offset of a distal end of the elongate outer tube is 12.7 mm (0.5 inches) or more, the offset measured perpendicular to the proximal longitudinal axis of the proximal portion.

The example tube delivery system may further comprise a damper disposed within an interior volume of the hand piece. The damper may comprise: a stationary housing, the stationary housing defines an annular channel with a closed bottom and an open top, the annular channel disposed around a longitudinal central axis, and the annular channel has a depth from the closed bottom to the open top measured parallel to the longitudinal central axis; a rotor defining a first arcuate vane and a second arcuate vane, the first and second arcuate vanes disposed in the annular channel; and a viscous fluid within the stationary housing and contacting the first and second arcuate vanes. In some cases, the viscous fluid is damping grease. The example tube delivery system may further comprise: a damping shaft defined by the rotor, the damping shaft protrudes from a first end of the damper, and the damping shaft coupled to the drive assembly; and a winding shaft defined by the rotor, the winding shaft protrudes opposite the damping shaft, and the winding shaft operationally exposed through the stationary housing.

In the example tube delivery system, the introducer may comprise polyetheretherkeytone (PEEK) having a wall thickness of 0.1016 mm (0.0040 inches) or less, and an outside diameter of 2.032 mm (0.080 inches) or less.

Another example is a method of installing a tympanostomy tube through a tympanic membrane, the method comprising: puncturing a tympanic membrane with a piercing element to create a myringotomy, the piercing element concentrically disposed within an introducer, the piercing element telescoped through a central lumen of a tympanostomy tube, and the tympanostomy tube abutting an interior diameter of the introducer; and then expanding the myringotomy by dilating a distal opening defined by a first leaf and a second leaf disposed on a distal end of the introducer; and retracting the introducer while simultaneously holding the tympanostomy tube in place through the myringotomy.

In the example method, expanding the myringotomy may further comprise translating the tympanostomy tube toward the distal end of the introducer, the tympanostomy tube dilates the first leaf and the second leaf.

In the example method, expanding the myringotomy may further comprise: separating the first leaf from the second leaf along a first longitudinal kerf, the first longitudinal kerf on a first side of the introducer between the first leaf and the second leaf; and simultaneously separating the first leaf from the second leaf along a second longitudinal kerf, the second longitudinal kerf on a second side between the first leaf and the second leaf. In some cases, prior to separation, the first longitudinal kerf and the second longitudinal kerf are co-planar with a longitudinal central axis of the introducer. In some cases: separating the first leaf from the second leaf along the first longitudinal kerf may further comprise widening a first circumferential kerf the intersects the first longitudinal kerf; and separating the first leaf from the second leaf along the second longitudinal kerf may further comprise widening a second circumferential kerf the intersects the second longitudinal kerf; wherein, prior to separation, the first circumferential kerf and the second circumferential kerf are coplanar, and a plane defined by the first and second circumferential kerfs is perpendicular to a longitudinal central axis of the introducer.

In the example method, expanding the myringotomy may further comprise: translating the tympanostomy tube toward the distal end of the introducer; separating, by the tympanostomy tube, the first leaf from the second leaf along a first longitudinal kerf, the first longitudinal kerf on a first side of the introducer between the first leaf and the second leaf; and simultaneously separating, by the tympanostomy tube, the first leaf from the second leaf along a second longitudinal kerf, the second longitudinal kerf on a second side between the first leaf and the second leaf. In some cases, prior to separation, the first longitudinal kerf and the second longitudinal kerf are co-planar with a longitudinal central axis of the introducer. In the method: separating the first leaf from the second leaf along the first longitudinal kerf may further comprise widening a first circumferential kerf the intersects the first longitudinal kerf; separating the first leaf from the second leaf along the second longitudinal kerf may further comprise widening a second circumferential kerf the intersects the second longitudinal kerf; and wherein, prior to separation, the first circumferential kerf and the second circumferential kerf are coplanar, and a plane defined by the first and second circumferential kerfs is perpendicular to the longitudinal central axis of the introducer.

Prior to puncturing, expanding, and retracting, the example method may further comprise winding a torsion spring by turning a rotor of a damper coupled to a drive assembly, the drive assembly configured to translate the piercing element and the introducer relative to an elongate outer tube. During the puncturing, expanding, and retracting, the example method may further comprise controlling rotational speed of a cam of the drive assembly, the controlling by the damper.

BRIEF DESCRIPTION OF THE DRAWINGS

For a detailed description of example embodiments, reference will now be made to the accompanying drawings in which.

DEFINITIONS

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple"

or “couples” is intended to mean either an indirect or direct connection. Thus, if a first device couples to a second device, that connection may be through a direct connection or through an indirect connection via other devices and connections.

“About” in reference to a recited value shall mean the recited value plus or minus 5% of the recited value.

Various apertures may be referred to a “bore,” or “through bore” or “counter bore.” Reference to a bore, through bore, or counter bore shall not be read to imply that any such bore, through bore, or counter bore is created by boring or drilling. The bore, through bore, or counter bore may be created in any suitable fashion.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various embodiments are directed to tube delivery systems, and methods of operating and using tube delivery systems, such as used in performing a tympanostomy. More particularly, at least one example embodiments is directed to a tube delivery system comprising an elongate shaft extending from a hand piece, and the elongate shaft is curved or offset so as to reduce the hand piece or the clinician’s hand from interfering with the line-of-sight to the target treatment area. Another example embodiment may comprise a trigger mechanism that reduces or eliminates mechanical sound associated with the tube delivery system performing a myringotomy and installing a tympanostomy tube. Yet another example embodiment is directed to a multi-piece cam assembly within the tube delivery system that reduces the cost of the tube delivery system, and thus reduces the cost of tympanostomy procedures. Each of these example embodiments may be implemented alone or in any combination. The specification now turns to a high level system overview.

Figures 1, 2:
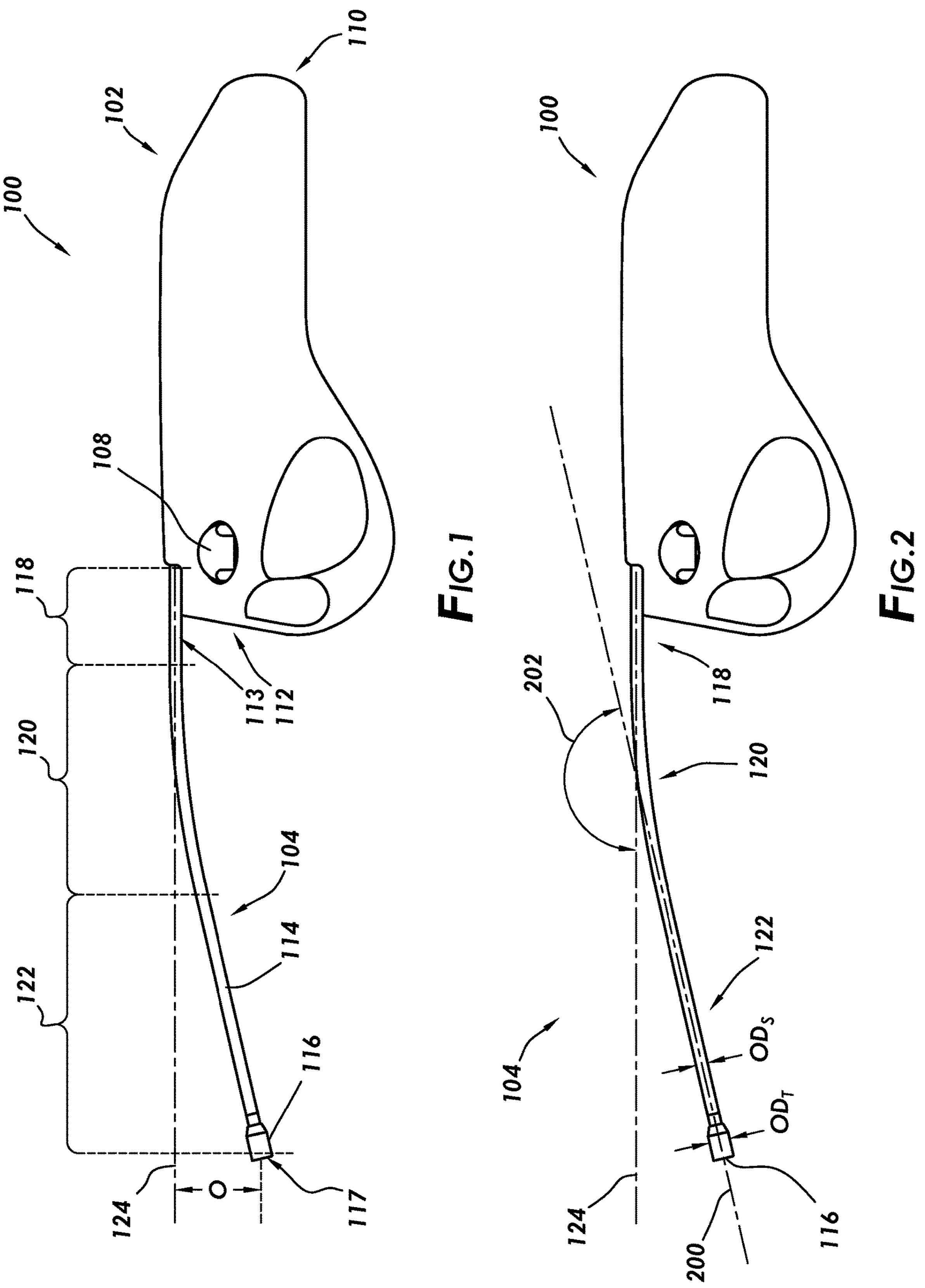
FIG. 1 shows a side elevation view of a tube delivery system in accordance with at least some embodiments.
FIG. 2 shows a side elevation view of a tube delivery system in accordance with at least some embodiments.

FIG. 1 shows a side elevation view of a tube delivery system in accordance with at least some embodiments. In particular, FIG. 1 shows the example tube delivery system 100 comprising a hand piece body or hand piece 102 and a shaft assembly 104. The hand piece 102 defines an internal volume (not visible in FIG. 1), and the shaft assembly 104 extends into the internal volume of the hand piece 102. Visible through an aperture of the hand piece 102 is a pushbutton 108 that a clinician uses to trigger a drive assembly disposed within the internal volume of the hand piece 102. The relationship between the pushbutton 108 and the drive assembly is discussed in greater detail below.

The hand piece 102 defines a proximal end 110 and a distal end 112. Similarly, the shaft assembly 104 defines a proximal end 113 and a distal end 117. It follows the proximal end 113 of the shaft assembly 104 is coupled to the distal end 112 of the hand piece 102. Throughout the specification, locations of components and movements of components may be described in relative terms proximal and distal. For example, a component may be described as being “distal” to a particular feature, and thus the component may be on the distal side of the particular feature or closer to the distal end (e.g., distal end 117). Similarly, a component may be describes as moving “distally,” and thus the component may move toward the distal end of the particular feature or of the overall device. As a more specific example of relative placement, the shaft assembly 104 comprises an elongate outer tube 114 that extends from the distal end 112 of the hand piece 102. Disposed on the distal end 117 of the shaft assembly 104 is a tip 116.

In example embodiments, the tip 116 is made of a clear plastic or transparent material to help with visualization of the tympanic membrane. The tip 116 may extend about 0.130 inches (about 3.3 mm) beyond the distal end of the elongate outer tube 114. In example embodiments the tip 116 is molded in place (e.g., over molded). Over molding, compared to other coupling techniques such as use of adhesives, reduces labor cost for assembly and simplifies the tolerance considerations. Moreover, the length of the tip 116 reduces binding between the introducer (discussed more below) and the inside diameter of the elongate outer tube 114 as the introducer dilates a myringotomy during placement of a tympanostomy tube.

Externally, the shaft assembly 104 can be conceptually divided into a proximal straight section 118, a curved section 120, and a distal straight section 122. The proximal straight section 118 ensures the shaft assembly 104 is properly aligned with drive assembly (not visible) disposed within the hand piece 102. An example drive assembly is discussed in greater detail below. The distal straight section 122 is designed and constructed to have sufficient length to telescope through a speculum (not shown) used for otologic procedures. The curved section 120 is curved to provide a bend angle such that the distal tip is offset from by a predetermined distance O measured from a longitudinal central axis 124 of the proximal straight section 118. In example cases, the proximal straight section 118 has length of about 1 inch (about 25.4 mm), the curved section 120 has a length of about 1.9 inches (about 48.26 mm) measured along the arc, and the distal straight section 122 has a length of about 1.475 inches (about 37.465 mm). These example lengths result in an example offset O of about 0.55 inches (about 13.97 mm). The recited lengths are merely an example, and other suitable lengths may be selected depending on a variety of factors, such as the desired offset O and the expected length of the speculum. In some cases, the length of the distal straight section 122 and the arc length of the curved section 120 may be related (at a particular bend radius) to achieve a desired offset. In one example case, the ratio of the length of the distal straight section 122 over the arc length of the curved section 120 is about 0.8 or less for a bend radius of about 8.3 inches (about 210.8 mm) below the center line.

FIG. 2 shows a side elevation view of a tube delivery system in accordance with at least some embodiments. In particular, FIG. 2 shows the tube delivery 100 of FIG. 1 to explain the various relationships of the shaft assembly 104 in a different context. In particular, the shaft assembly 104 includes the proximal straight section 118 defining a longitudinal central axis 124. The distal straight section 122 defines a longitudinal central axis 200. The curved section 120 is disposed between the proximal straight section 118 and the distal straight section 122. In the example system, the obtuse angle 202 between the longitudinal central axis 124 axis and the longitudinal central axis 200 is between and including 170 angular degrees and 160 angular degrees.

FIG. 2 also shows that the shaft assembly 104 has an outside diameter $OD_S$. The outside diameter $OD_S$ is shown with respect to the distal straight section 122, but it will be understood that outside diameter $OD_S$ may extend along the length of the shaft assembly 104, with the exception of the tip 116, which may have a slightly larger outside diameter $OD_T$ owing to the over molded construction. In example embodiments, the elongate outer tube 114 has an outside diameter $OD_S$ of about 0.076 inches (about 1.93 mm), and the example distal tip 116 has an $OD_T$ owing of about 0.091 inches (about 2.31 mm). In prior generations of the tube delivery system designed by the inventors of the current specification, the elongate outer tube had a larger outside diameter, on the order of about 0.085 inches (about 2.16 mm). Similarly, in the prior generations of the tube delivery system designed by the inventors of the current specification, the tip had a larger outside diameter, on the order of about 0.099 inches (about 2.51 mm). While the change in outside diameters is small in a measurement sense, the smaller outside diameters increase visibility substantially because the viewing area through a distal end of a speculum occupied by the elongate outer tube decreases with square of the radius. The example change in outside diameter of the elongate outer tube 114 given above may make the cross-sectional area of the elongate outer tube 20% smaller, which may result in an increase in the visible area through the distal end of a speculum by about 8-10%.

Still referring to FIG. 2, disposed within the elongate outer tube 114 near the tip 116 is a tympanostomy tube that is not visible in FIG. 2. In use, a clinician places the tip 116 near, in apposition with, or abutting a tympanic membrane of a patient. Thereafter, the clinician triggers tube delivery system 100 by actuation of the pushbutton 108. Once actuated, the example tube delivery system 100 is designed and constructed to pierce the tympanic membrane (i.e., perform a myringotomy), dilate the myringotomy, and install the tympanostomy tube. In some example systems the piercing, dilating, and installation takes place in 500 milliseconds (ms) or less, and in a particular case about 150 ms. The specification now turns to a more detailed discussion of the shaft assembly 104 and the drive assembly within the hand piece 102.

Figure 3:
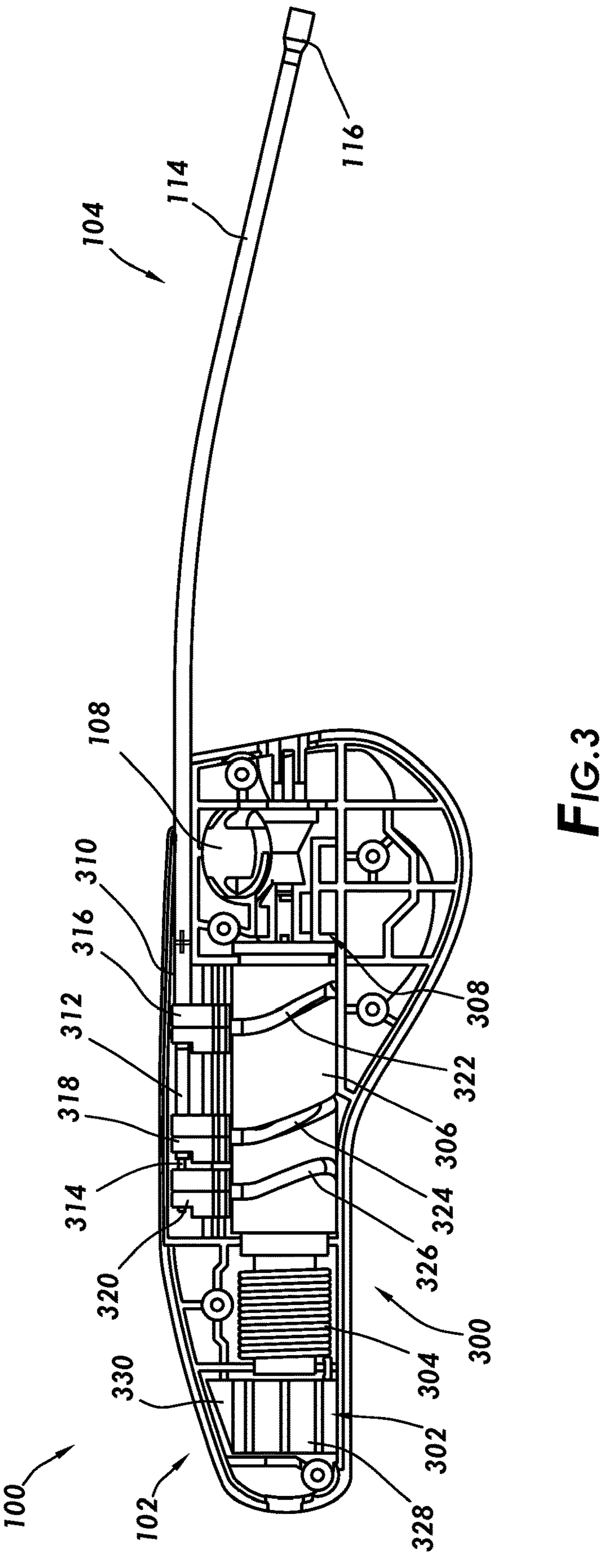
FIG. 3 shows a side elevation view of an example tube delivery system with a portion of the hand piece removed to show various components of the drive assembly, and in accordance with at least some embodiments.

FIG. 3 shows a side elevation view of an example tube delivery system 100 with a portion of the hand piece removed to show various components of the drive assembly. In particular, FIG. 3 shows the example tube delivery system 100 comprises the hand piece 102 and the shaft assembly 104. Disposed within the hand piece 102 is the proximal end of the shaft assembly 104, along with various components of the drive assembly 300. The example drive assembly 300 comprises, working from left to right in the figure, a damper assembly 302, a torsion spring 304, a cam assembly 306, and a drive actuation assembly 308 (that includes the push pushbutton 108). The discussion continues with a more detailed description of the shaft assembly 104.

Concentrically disposed within the elongate outer tube 114 is an introducer tube 310 (hereafter just introducer 310), a pusher 312, and a cutter or piercer 314. Also disposed at the distal end of the elongate outer tube 114 is a tympanostomy tube (not visible). The introducer 310 is coupled on its proximal end to a cam follower 316. The pusher 312 is coupled on its proximal end to a cam follower 318. The piercer 314 is coupled on its proximal end to a cam follower 320. Each cam follower is associated with a cam track, external groove, or annular groove in the cam assembly 306. More specifically, cam follower 316 is coupled to and associated with the annular groove 322. Cam follower 318 is coupled to and associated with the annular groove 324. And cam follower 320 is coupled to and associated with the annular groove 326.

During assembly of the tube delivery system 100, the torsion spring 304 is wound and the drive actuation assembly 308 is arranged to hold the cam assembly against rotation. During an otologic procedure, when the tip 116 is adjacent to or in apposition with the tympanic membrane of the patient, the clinician actuates the pushbutton 108 which enables the cam assembly 306 to turn based on rotational force provided by the torsion spring 304. As the cam assembly turns, the cam followers 316, 318, and 320 move relative to the elongate outer tube 114 and/or the hand piece 102 based on the respectively cam followers moving in respective annular grooves (discussed more below). Thus, rotation of the cam assembly 306 moves the piercer 314, the introducer 310, and the pusher 312 to implement the piercing and dilating of the tympanic membrane, and the placement of the tympanostomy tube.

Figure 4:
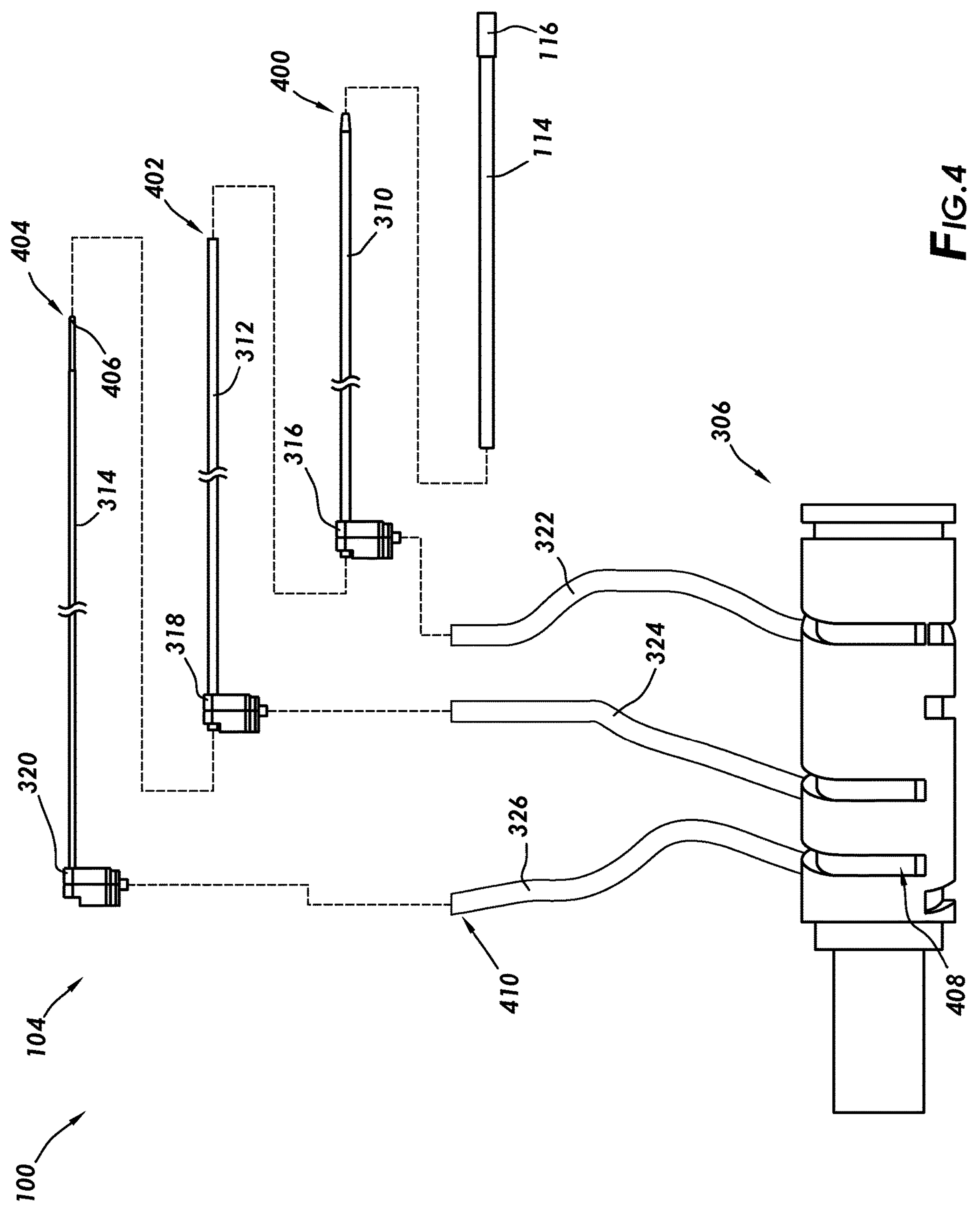
FIG. 4 shows an exploded view of the shaft assembly, along with a side elevation view of the cam assembly, in accordance with at least some embodiments.

FIG. 4 shows an exploded view of the shaft assembly 104, along with a side elevation view of the cam assembly 306, in accordance with at least some embodiments. The various components of the shaft assembly 104 are shown straight rather than curved so as not to unduly complicate the figure. FIG. 4 also shows the annular grooves "rolled out" flat to show relative positions of the annular grooves during rotation of the cam assembly 306. Turning first to the example shaft assembly 104, FIG. 4 shows an example elongate outer tube 114 comprising the clear distal tip 116. Concentrically disposed within the elongate outer tube 114 is the introducer 310. The distal end 400 of the introducer 310 defines a plurality of flexible leaves, the flexible leaves discussed in greater detail below. In a non-triggered state prior to deployment, the distal end 400 of the introducer 310 extends past a distal end of the elongate outer tube 114, and the distal end 400 extends into an internal volume defined by the tip 116. The cam follower 316 for the introducer 310 is coupled on the proximal end of the introducer 310, and the cam follower 318 is in operational relationship with the annular groove 322.

Concentrically disposed within the introducer 310 is the pusher 312. In a non-triggered state prior to deployment, the distal end 402 of the pusher 312 terminates proximally from the distal end 400 of the introducer 310. In particular, in example cases the distal end 402 of the pusher 312 is close to or abuts a proximal end of the tympanostomy tube (not shown) disposed within the introducer 310. The cam follower 318 for the pusher 312 is coupled on the proximal end of the pusher 312, and the cam follower 318 is in operational relationship with the annular groove 324.

Concentrically disposed within the pusher 312 is the piercer 314. The distal end 404 of the piercer 314 defines a blade or piercing element 406. In example cases, in a non-triggered state prior to deployment the distal end 404 of the piercer extends past the distal end 400 of the introducer 310 and into the internal volume defined by the tip 116. The cam follower 320 for the piercer 314 is coupled on the proximal end of the piercer 314, and the cam follower 320 is in operational relationship with the annular groove 326. The example piercer 314 may be an elongate cylinder or rod to have sufficient strength to pierce the tympanic membrane. In some cases, the piercer 314 may be constructed of a metallic material. In cases in which curved section provides even greater offset of the distal tip, the piercer 314 may be made of the metallic material referred to as Nitinol. Moreover, in the non-triggered state prior to deployment the piercer 314 in the example form of a rod may extend through a central lumen of a tympanostomy tube (not shown) disposed within the introducer 310.

Still referring to FIG. 4, the annular grooves 322, 324, and 326 are shown "rolled out" flat to illustrate relative positions of the annular grooves during rotation of the cam assembly 306. Referring to annular groove 326 as representative, in the non-triggered state prior to deployment the cam follower 320 reside in the annular groove 326 at the initial location 408. Once the tube delivery system is triggered, the cam assembly 306 turns, and the cam follower 320 translates along and within annular groove 326. As the cam follower 320 translates along and within the annular groove 326, the cam follower 320 and piercer 314 change axial position relative to the stationary elongate outer tube 114. Ultimately, at the end of the rotation of the cam assembly 306, the cam follower 320 resides at the end location 410. More generally then, the cam followers translate along and within their respective annular grooves. The translations results in axial movement of the various members of the shaft assembly 104, including relative movements, to implement piercing of the tympanic membrane and installation of the tympanostomy tube across the tympanic membrane. Before describing the relative movements in greater detail, the specification turns to a more detailed description of the components of the shaft assembly 104.

Figure 5:
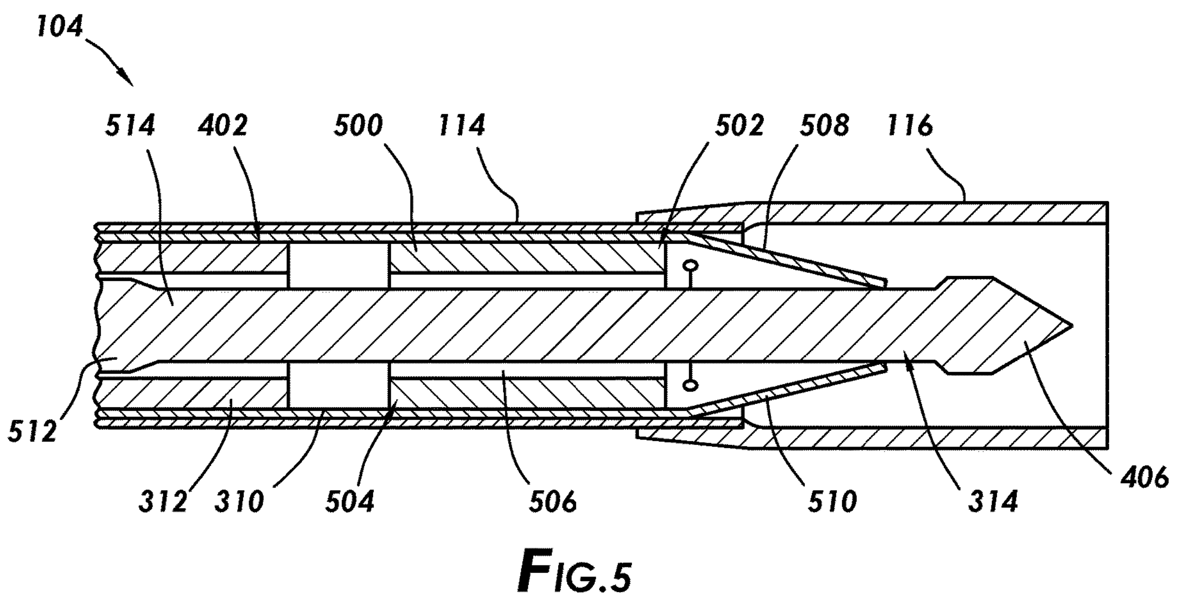
FIG. 5 shows a cross-sectional elevation view of a distal end of the shaft assembly in accordance with at least some embodiments.

FIG. 5 shows a cross-sectional elevation view of a distal end of the shaft assembly 104 in accordance with at least some embodiments. In particular, FIG. 5 shows the elongate outer tube 114 with the tip 116 coupled to the distal end of the elongate outer tube 114. The tip 116 defines an internal volume between the distal end of the elongate outer tube 114 and the open distal end of the tip 116. Concentrically disposed within the elongate outer tube 114 is the introducer 310. The introducer 310 defines an outside diameter slidingly engaged with the inside diameter of the elongate outer tube 114. The introducer 310 also defines an inside diameter. Disposed within the inside diameter of the introducer 310 is a tympanostomy tube 500. The tympanostomy tube 500 defines a distal end 502, a proximal end 504, and central lumen 506. More particularly, the tympanostomy tube 500 is disposed within and abutting the inside diameter of the introducer 310. In some example cases, the tympanostomy tube 500 defines a flange on the distal end 502, and a flange on the proximal end 504, and when within the inside diameter of the introducer 310 the flanges are in a compressed state folded back onto the outside surface of the central lumen 506.

The example introducer 310 defines on its distal end a plurality of leaves that form a cone or taper pointing toward the distal end. In one particular example, the introducer 310 defines two leaves. In the cross-sectional view of FIG. 5, a portion of each example leaf is shown as leaf 508 and leaf 510. In the non-triggered state prior to deployment, the example tympanostomy tube 500 abuts the inside diameter of the introducer 310 proximally of the leaves 508 and 510. The leaves are discussed in greater detail below after a discussion of the piercer 314 and pusher 312.

The example shaft assembly 104 further comprises the pusher 312. The pusher 312 is concentrically disposed within the introducer 310, and thus also concentrically disposed within the elongate outer tube 114. The pusher 312 defines an outside diameter slidingly engaged with the inside diameter of the introducer 310. Moreover, the example pusher 312 defines an inside diameter through which the piercer 314 telescopes. In alternative cases in which the piercer 314 is omitted in favor of other piercing techniques (e.g., separate piercing instrument, or the introducer 310 itself pierces directly), the pusher 312 may be implemented as a solid cylinder or rod with no internal lumen. In the non-trigger state prior to deployment of the tympanostomy tube 500, the distal end 402 of the pusher 312 resides proximally from the proximal end 504 of the tympanostomy tube 500. In some cases, and as shown, the pusher 312 defines a setback distance (e.g., a few millimeters). In other cases, however, in the non-trigger state prior to deployment of the tympanostomy tube 500 the distal end 402 of the pusher 312 may touch or abut the proximal end 504 of the tympanostomy tube 500.

Still referring to FIG. 5, the example shaft assembly 104 further comprises the piercer 314. The piercer 314 is concentrically disposed within the pusher 312, and thus also concentrically disposed within the introducer 310 and the elongate outer tube 114. The example piercer 314 defines multiple portions with varying outside diameters. For example, the piercer 314 defines proximal portion 512, a piercing element 406 on the distal end of the piercer 314, and a medial portion 514 medially disposed between the proximal portion 512 and the piercer element 406. The example proximal portion 512 defines an outside diameter that is slidingly engaged with the inside diameter of the introducer 310. The medial portion 514 has an outside diameter that is smaller than the outside diameter of the proximal portion 512. In example cases, the outside diameter of the medial portion 514 telescopes through the central lumen 506 of the tympanostomy tube 500. In one example case, the outside diameter of the medial portion 514 is smaller than the inside diameter of the central lumen 506 of the tympanostomy tube 500 to reduce friction. In other cases, however, the outside diameter of the medial portion 514 is designed and constructed to abut the inside diameter of the central lumen 506 of the tympanostomy tube 500 to support the tympanostomy tube 500 during periods when the tympanostomy tube 500 is translating distally within the introducer 310 and dilating the leaves of the introducer 310 (discussed more below). The piercing element 406 on the distal end of the piercer 314 resides beyond the distal end of the elongate outer tube 114, beyond the distal end of the introducer 310, and within the internal volume defined by the tip 116.

Figure 6:
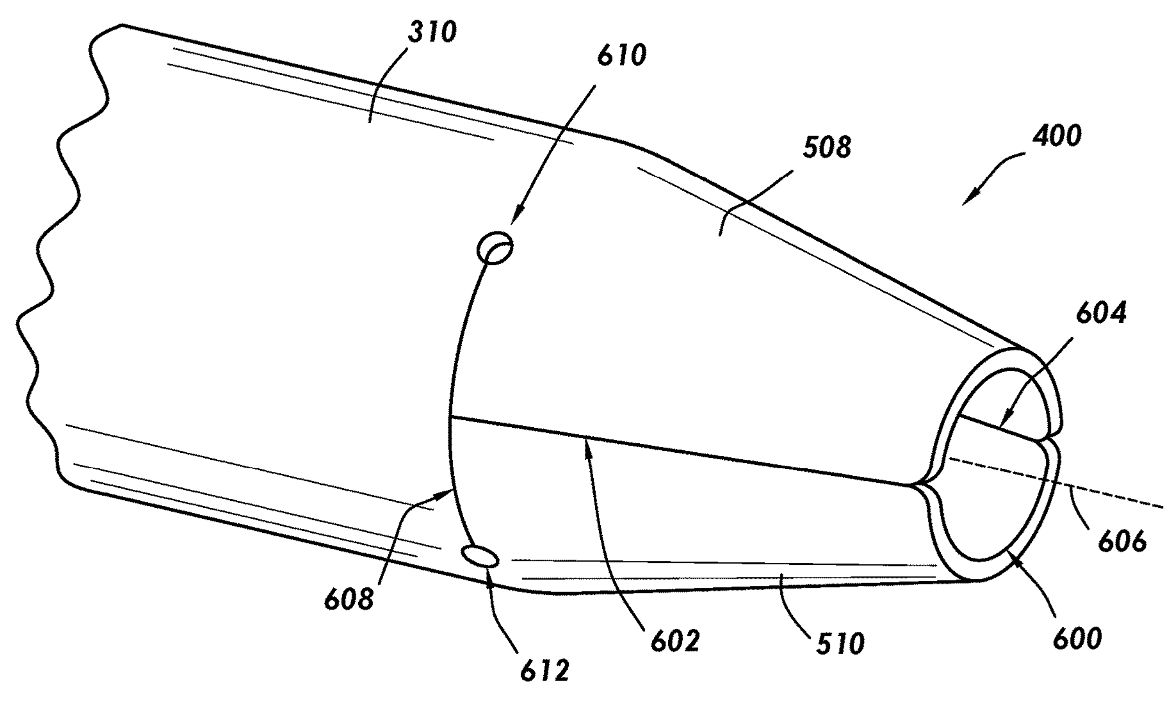
FIG. 6 shows a perspective view of the distal end of the introducer in accordance with at least some embodiments.

FIG. 6 shows a perspective view of the distal end of the introducer 310. In particular, the example introducer 310 defines the distal end 400 comprising the leaf 508 and the leaf 510. The leaf 508 and the leaf 510 form a taper, with the widest portion at the proximal end of the taper and terminating in narrow portion defining a distal aperture 600. Stated differently, the leaves 508 and 510 form the shape of a conic frustum, with the wider portion at the outside diameter of the cylindrical portion of the introducer, and the narrow portion defining the distal aperture 600. In example cases, the outside diameter of the introduce 310 at the distal end is smaller than an outside diameter of the piercer 406 to enable the introducer the slip into the incision made by the piercer 406. In the non-triggered state prior to deployment, the distal aperture 600 defines a diameter that abuts the outside diameter of the medial portion 514 (not shown) of the piercer 314. In one example case, the diameter of the distal aperture 600 prior to dilation may be about 0.028 inches (about 0.71 mm).

In the example system, the leaves 508 and 510 are defined by cuts or kerfs through the material of the introducer 310. In particular, the example introducer 310 comprises a longitudinal kerf 602 on a first side of the introducer 310, and a longitudinal kerf 604 on a second side of the introducer 310. In one sense, the longitudinal kerfs 602 and 604 can be said to reside between the leaves 508 and 510. In another sense, the longitudinal kerfs 602 and 604 can be said to define the leaves 508 and 510 within the frustum-shaped taper. In one example case, and as shown, the longitudinal kerf 602 and the longitudinal kerf 604 are co-planar, may also be coplanar with a longitudinal central axis 606 of the introducer 310. Depending on the flexibility of the material that forms the introducer 310, the longitudinal kerfs 602 and 604 alone may be sufficient to enable the introducer 310 to expand the myringotomy and enable the tympanostomy tube to be deployed through the distal end 400 of the introducer. However, in yet still further embodiments additional kerfs are present to enable dilation the leaves 508 and 510.

In example embodiments one or both of the longitudinal kerfs may also be associated with a respective circumferential kerf. For example, FIG. 6 shows a circumferential cut or circumferential kerf 608 that intersects a proximal end of the longitudinal kerf 602. Though not visible in the view of FIG. 6, the longitudinal kerf 604 may likewise be associated with circumferential kerf that intersects a proximal end of the longitudinal kerf 604, though it is noted that such a circumferential kerf is partially visible in the cross-sectional view of FIG. 5. The example circumferential kerf 608 partially circumscribes the outside diameter of the introducer 310. Likewise, the circumferential kerf associated with the longitudinal kerf 604 partially circumscribes the outside diameter of the introducer 310. In one example case, the circumferential kerf 608 and the corresponding circumferential kerf associated with longitudinal kerf 604 are coplanar, and a plane defined by the circumferential kerfs is perpendicular to the longitudinal central axis 606 of the introducer 310. Again depending on the flexibility of the material that forms the introducer 310, the combined longitudinal and circumferential kerfs alone may be sufficient to enable the introducer 310 to expand the myringotomy and enable the tympanostomy tube to be deployed through the distal end 400 of the introducer 310. However, in yet still further embodiments additional strain relief mechanism are used to enable dilation the leaves 508 and 510 without catastrophic damage (e.g., cracking and/or flaking) of the introducer 310.

One or both of the circumferential kerfs may also be implemented in association with the strain relief apertures. Referring to circumferential kerf 608 as representative, FIG. 6 shows a strain relief aperture 610 at a first end of the circumferential kerf 608, and a strain relief aperture 612 at the opposite end of the circumferential kerf 608. The circumferential kerf associated with longitudinal kerf 604 that is not visible in FIG. 6 may likewise be associated with strain relief apertures on each end, though it is noted that such a circumferential kerf and associated strain relief apertures are partially visible in the cross-sectional view of FIG. 5.

Referring to longitudinal kerf 602 and associated circumferential kerf 608 as representative, the kerfs 602 and 608 for a “T”-cut pattern to enable the leaves 508 and 510 to open or dilate as the tympanostomy tube is advanced through the introducer 310. Moreover, the “T”-cut pattern reduces force used to dilate the leaves 508 and 510, which as discussed more below is provided most directly by the tympanostomy tube. Further still, using two “T”-cut patterns to form two leaves 508 and 510 also reduces distortion of the expanded section of the introducer 310 ensuring that the introducer 310 can be translated back into the elongate outer tube after deployment of the tympanostomy tube. Utilizing two “T”-cut patterns reduces non-circularity of the distal end 400 of the introducer 310, particularly during insertion into and dilation of the tympanic membrane, and delivery of the tympanostomy tube across the tympanic membrane.

Figure 7:
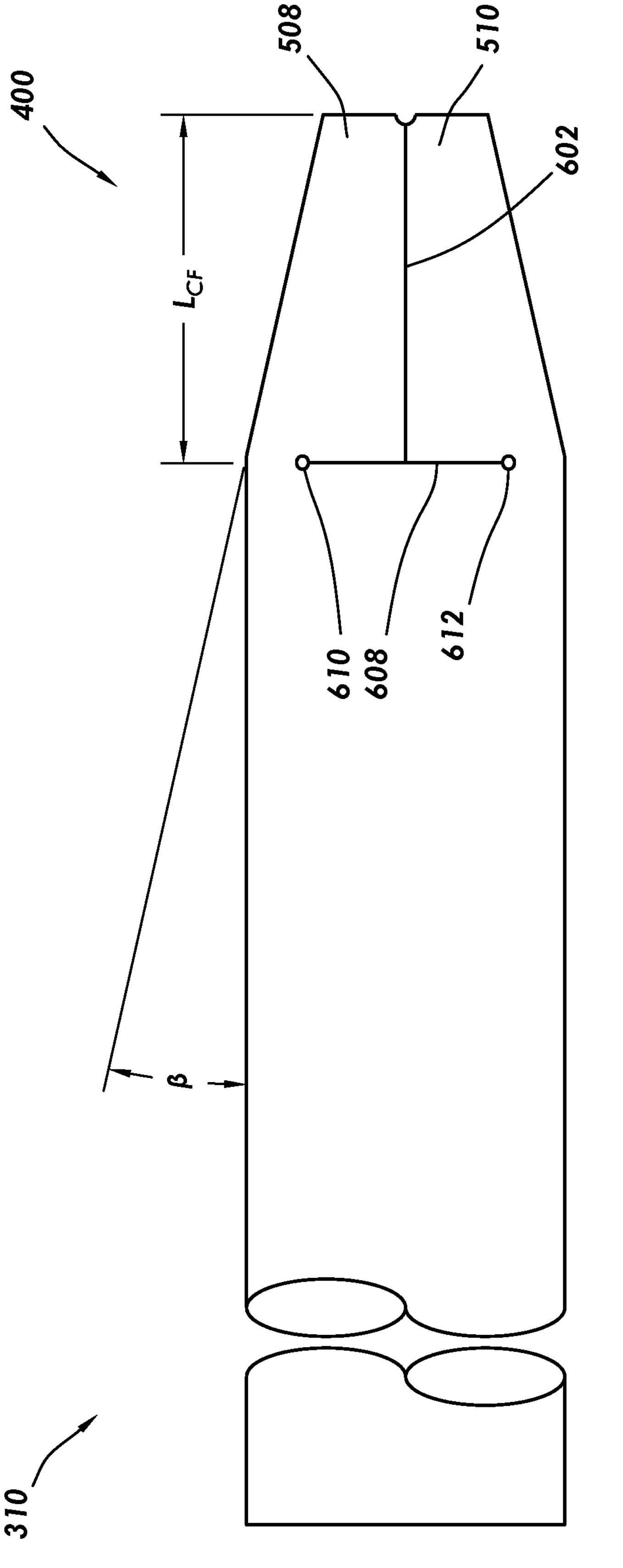
FIG. 7 shows a side elevation view of an introducer in accordance with at least some embodiments.

FIG. 7 shows a side elevation view of the introducer 310. In particular, FIG. 7 shows the example longitudinal kerf 602 intersecting the circumferential kerf 608. The example strain relief apertures 610 and 612 are disposed at opposite ends of the circumferential kerf 608. The various visible kerfs, as well as a correspondence set of kerfs on the opposite side, thus define the leaves 508 and 510. In one example case, the introducer 310 is made of a thin-wall polyetheretherketone (PEEK) to have sufficient strength to expand the myringotomy, but also to be operation in the bent or curved configuration of the shaft assembly 104 (FIG. 1). PEEK also has sufficient lubricity with the respect to the material of the tympanostomy tube to enable the tympanostomy tube to slide within introducer 310

In some cases the introducer 310 is an extruded component. After extrusion, the extruded component takes the form a right circular cylinder, and thereafter the taper or conic frustum shape of the distal end 400 is created in a further forming process. That is, the distal end is placed in a die or mold and further heated to create the conic frustum shape. Inasmuch as the thickness of the leaves is about the same as the wall thickness of the cylindrical portion (e.g., about 0.0030 inches, or about 0.0762 mm), in the forming process the conic frustum shape lengthens and the excess material is cut off to form the distal tip. In one example case, the conic frustum shape has a length $L_{CF}$ of about 0.072 inches (about 1.83 mm). The side walls of the conic frustum shape form an angle β of about 25 angular degrees with respect to the outside surface of the cylindrical portion.

The example kerfs are laser cut to produce narrow kerf gaps, on the order of about 0.002 to 0.005 inches (about 0.05 to 0.13 mm). Narrow kerfs enable the tympanostomy tube to be the component that expands or dilates the leaves 508 and 510 while reducing or eliminating extrusion of the tympanostomy tube through the cuts during the initial dilation process. Depending on the material of the introducer 310 and the material of the tympanostomy tube, the kerf gaps may be wider, and thus the kerfs may be created using other techniques, such as cutting by way of a mechanical blade system. Use of PEEK as the introducer material is merely an example, and in other cases a thin-walled metallic material may be used. In order to accommodate the bend or curve of the shaft assembly, the thin-walled metallic material may implement a series of relief cuts on alternating sides of the introducer. Before proceeding, it is noted that the more leaves are possible (e.g., three leaves, four leaves), and thus additional kerfs may be present.

Figure 8:
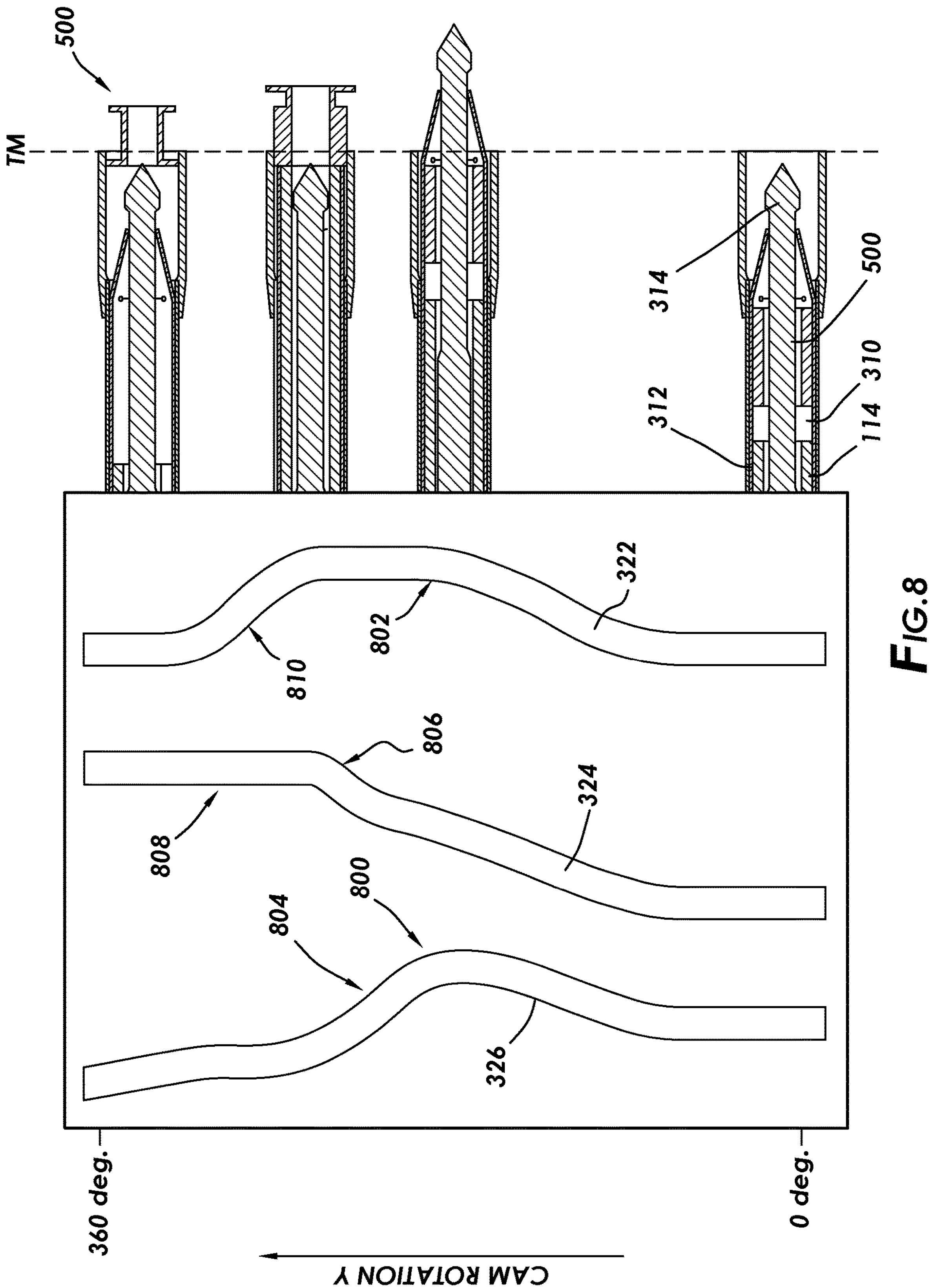
FIG. 8 shows a conceptual view of a relationship between the annular grooves of the cam assembly, and installation of a tympanostomy tube across tympanic membrane, in accordance with least some embodiments.

FIG. 8 shows a conceptual view of a relationship between the annular grooves of the cam assembly, and installation of a tympanostomy tube across tympanic membrane. In particular, FIG. 8 shows annular grooves 322, 324, and 326 associated with the introducer 310, the pusher 312, and the piercer 314, respectively. In the non-triggered condition, represented as the zero degree point in the figure, the various components at the distal end of the tube delivery system are as discussed with respect to FIG. 5, and a portion of FIG. 5 is reproduced in FIG. 8 along the same horizontal position as the zero degree point. FIG. 8 further shows the distal end of the tube delivery system in relationship to a tympanic membrane TM represented by the vertical dashed line.

Once triggered by the clinician, the cam assembly turns and the cam followers move along their respective annular grooves 322, 324, and 326. In the conceptual view of FIG. 8, rotation of the cam is shown by movement upward on the page. Initially the introducer 310, the pusher 312, and the piercer 314 move in unison, along with the tympanostomy tube 500 carried by the introducer 310. As the piercer 314 moves distally relative to the stationary elongate outer tube 114, the piercer 314 eventual pierces the tympanic membrane. The initial contact of the piercer 314 with the tympanic membrane is not shown so as not to unduly complicate the figure. As the piercer 314 and introducer 310 continue to move distally together, the leaves of the introducer 310 also extend partially through the tympanic membrane. The distal-most travel point of the piercer 314 is at point 800 of the annular groove 326. Similarly, the distal-most travel point of the introducer 310 is at point 802 of the annular groove 322.

As the cam assembly continues to rotate, the piercer 314 begins to withdraw or move proximally relative to the stationary elongate outer tube 114, and as shown in the area 804 of the annular groove 326. The introducer 310 remains at a relatively constant distal position while the pusher 312 continues to move distally, as shown in area 806 of the annular track 324. Thus, the pusher 312 translates the tympanostomy tube 500 toward the distal end of the introducer 310, and eventually pushes the distal end of the tympanostomy tube 500 to and through the leaves of the introducer 310. Pushing the tympanostomy tube through the leaves both dilates the distal open end of the introducer, and also expands the myringotomy initially created by the piercer 314. Stated differently, pushing the tympanostomy tube through the leaves separates the leaves along longitudinal kerfs, widens the gaps of the circumferential kerfs, and simultaneously expands the myringotomy. As the distal end of the tympanostomy tube 500 clears the distal end of the introducer 310, the example tympanostomy tube 500 has a flange that expands open as shown in FIG. 8.

Eventually the pusher 312 reaches its distal-most point, as shown in the area 808 of the annular groove 324. In the example embodiments shown, the pusher 312 remains at its distal-most point or configuration for the balance of the rotation of the cam assembly. While the pusher 312 remains at its distal-most configuration, the introducer withdraws or moves proximally relative to the stationary elongate outer tube 114, as shown in the area 810 of the annular groove 322. Thus, the introducer 310 withdraws as the pusher 312 holds the tympanostomy tube 500 in place across the tympanic membrane. Holding the tympanostomy tube 500 in place across the tympanic membrane in the example embodiments may mean holding the tympanostomy tube 500 against withdrawing out of the myringotomy along the longitudinal axis of the introducer 310. Eventually, the introducer 310 withdraws sufficiently to clear the proximal end of the tympanostomy tube 500, at which point a proximal flange may expand, as shown in FIG. 8. Thereafter, the clinician removes the tube delivery system from the ear canal, and the tympanostomy tube 500 remains in place across the tympanic membrane. The specification now turns to an example cam assembly.

Returning briefly to FIG. 3. FIG. 3 shows the cam assembly 306 comprising the annular grooves 322, 324, and 326. The cam assembly 306 couples on its proximal end to the torsion spring 304 by way of a reduced diameter portion. That is, the torsion spring 304 is concentrically arranged over the reduced diameter portion. The distal end of the cam assembly 306 is couple to the drive actuation assembly 308. In related-art devices, the cam may be implemented as a single-piece and/or integrated component. However, the cost of manufacture of the single-piece component (e.g., manufacture by way of Swiss-screw machine) may be high relative to the total parts and manufacturing cost of the tube delivery system 100. In order to reduce overall cost, in example embodiments the cam assembly 306 is a multi-piece component.

Figure 9:
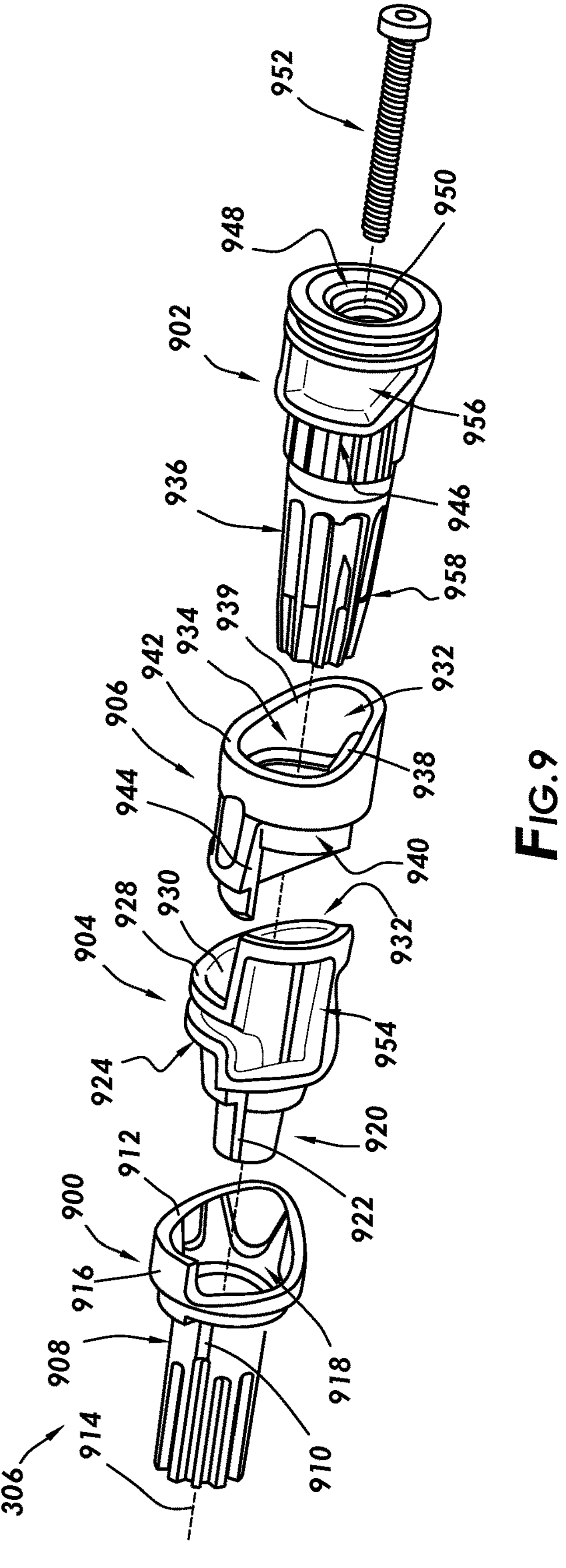
FIG. 9 shows an exploded perspective view of a cam assembly in accordance with at least some embodiments.

FIG. 9 shows an exploded perspective view of a cam assembly 306 in accordance with at least some embodiments. In particular, visible in FIG. 9 is proximal cam member 900 and distal cam member 902. Disposed between the proximal cam member 900 and the distal cam member 902 are a medial cam member 904 and a medial cam member 906. The proximal cam member 900 defines a reduced diameter portion or spring support portion 908 that extends proximally. The spring support portion 908 is designed and constructed such that the torsion spring 304 (FIG. 3) telescopes over the spring support portion 908 and is concentrically arranged over the spring support 908. The torsion spring 304 couples to the proximal cam member 900 to supply rotational force, for example, couples at slot 910.

The example proximal cam member 900 further comprises an annular side wall 916 that defines a distal ridge that faces toward the distal end of the proximal cam member 900. For reasons that will become clearer below, the distal ridge of the annular side wall 916 is referred to as a slide surface or shoulder 912. The example annular side wall 916 has a height or length (measured parallel to the longitudinal central axis 914 of the cam assembly 306) that varies with radial location. In example embodiments, the shoulder 912 defines a first wall or first shoulder of the annular groove 326 (FIG. 3) associated with the piercer 314 (also FIG. 3). An inside surface of the annular side wall 916 defines an interior volume 918. The interior volume 918 defines a female plug portion into which a portion of the medial cam member 904 telescopes during assembly. In some example embodiments, the interior volume 918 defines one more features that help rotationally align the medial cam member 904 and/or lock or hold the medial cam member 904 rotationally fixed along the longitudinal central axis 914 relative to the proximal cam member 900.

The medial cam member 904 defines a rod or pin 920 that extends proximally. The pin 920 defines a male plug portion that telescopes into the interior volume 918 of the proximal cam member 900 during assembly. In some example embodiments, the pin 920 defines one more features that help rotationally align the medial cam member 904 and/or lock or hold the medial cam member 904 rotationally fixed along the longitudinal central axis 914 relative to the proximal cam member 900. For example, the pin 920 defines a trough or groove 922 on an outside surface of the pin 920. The groove 922 has an open top and a closed bottom, and defines a channel that is parallel to the longitudinal central axis 914. The groove 922 may mate with a corresponding ridge (not visible) defined in the interior volume 918 of the proximal cam member 900 to enable the rotational alignment and locking.

The medial cam member 904 further defines a slide surface or shoulder 924 medially disposed on the medial cam member 904, though in the perspective view of FIG. 9 the wall or shoulder is not visible. The example shoulder 924 has an axial location (relative to the longitudinal central axis 914) that varies with radial location. In the example system, shoulder 924 defines a surface that is a mirror image of the surface formed by shoulder 912 of the proximal cam member 900. The shoulder 924 defines a second wall or second side of the annular groove 326 (FIG. 3). Once the medial cam member 904 is assembled with the proximal cam member 900, shoulder 924 is spaced away or forms a gap with respect to the shoulder 912, thus forming the annular groove 326 (of FIG. 3).

The medial cam member 904 further comprises an annular side wall 930 that defines a distal ridge that faces toward the distal end of the medial cam member 904. The distal ridge of the annular side wall 930 is referred to as a slide surface or shoulder 928. The example annular side wall 930 has a height or length (measured parallel to the longitudinal central axis 914) that varies with radial location. In example embodiments, the shoulder 928 defines a first wall or first shoulder of the annular groove 324 (FIG. 3) associated with the pusher 312 (also FIG. 3). An inside surface of the annular side wall 930 defines an interior volume 932. The interior volume 932 defines a female plug portion into which a portion of the medial cam member 906 telescopes during assembly. In some example embodiments, the interior volume 932 defines one more features that help rotationally align the medial cam member 904 and/or lock or hold the medial cam member 904 rotationally fixed along the longitudinal central axis 914 relative to the medial cam member 904.

Still referring to the FIG. 9, and particularly the medial cam member 906. The medial cam member 906 defines a through bore or central lumen 934. As will be discussed in greater detail below, the central lumen 934 enables the rod or pin 936 of the distal cam member 902 to telescope through the medial cam member 906 and into the medial cam member 904 during assembly. In some example embodiments, the medial cam member 906 defines one more features on the proximal end that help rotationally align the medial cam member 906 and/or lock or hold the medial cam member 906 rotationally fixed along the longitudinal central axis 914 relative to the medial cam member 904. For example, the medial cam member 906 defines an alignment surface 944. The alignment surface 944 defines a plane that is coplanar with the longitudinal central axis 914. The alignment surface 944 abuts and aligns with a mating surface defined by the annular side wall 930 of the medial cam member 904 to enable the rotational alignment and locking.

The medial cam member 906 further defines a slide surface or shoulder 940 proximally disposed on the medial cam member 906, though in the perspective view of FIG. 9 the wall or shoulder is not visible. The example shoulder 940 has an axial location (with respect to the longitudinal central axis 914) that varies with radial location. In the example system, shoulder 940 defines a surface that is a mirror image of the surface formed by shoulder 928 of the medial cam member 904. The shoulder 940 defines a second side or second shoulder of the annular groove 324 (FIG. 3) of the pusher 312 (also FIG. 3). Once the medial cam member 906 is assembled with the medial cam member 904, shoulder 940 is spaced away or forms a gap with respect to the shoulder 928, thus forming the annular groove 324.

An annular side wall 939 of medial cam member 906 further defines a distal ridge that faces toward the distal end of the medial cam member 906. The distal ridge of the annular side wall 939 is referred to as a slide surface or shoulder 942. The example shoulder 942 has an axial location (with respect to the longitudinal central axis 914) that varies with radial location. In example embodiments, the shoulder 942 defines a first wall or first shoulder of the annular groove 322 (FIG. 3) associated with the introducer 310 (also FIG. 3). In some example embodiments, the central lumen 934 defines one more features that help rotationally align the medial cam member 906 and/or lock or hold the medial cam member 906 rotationally fixed along the longitudinal central axis 914 relative to the distal cam member 902. For example, the annular side wall 939 defines an internal protrusion or tab 938 on an inside surface of the central lumen 934 within the central lumen 934. The tab 938 forms a ridge that runs parallel to the longitudinal central axis 914. The tab 938 may mate with a corresponding groove (not visible) defined on the outside surface of the pin 936 of the distal cam member 902 to enable the rotational alignment and locking.

Still referring to the FIG. 9, and particularly the distal cam member 902. The distal cam member 902 defines the rod or pin 936 that extends proximally. The pin 936 defines a male plug portion that telescopes into the central lumen 934 of the medial cam member 906 during assembly. In some example embodiments, the pin 920 defines one more features that help rotationally align the distal cam member 902 and/or lock or hold the distal cam member 902 rotationally fixed along the longitudinal central axis 914 relative to the medial cam member 906. For example, the pin 936 may defines a trough or groove (not visible) on an outside surface of the pin 936 that mates with and rotationally aligns with the tab 938 of the medial cam member 906. Such a groove has an open top and a closed bottom, and defines a channel that is parallel to the longitudinal central axis 914.

The distal cam member 902 further defines a slide surface or shoulder 946 medially disposed on the distal cam member 902, though in the perspective view of FIG. 9 the wall or shoulder is not visible. The shoulder 946 faces the proximal direction. The example shoulder 946 has an axial location (with respect to the longitudinal central axis 914) that varies with radial location. In the example system, shoulder 946 defines a surface that is a mirror image of the surface formed by shoulder 942 of the medial cam member 906. The shoulder 946 defines a second wall or second shoulder of the annular groove 322 (FIG. 3) associated with the introducer 310 (also FIG. 3). Once the distal cam member 902 is assembled with the medial cam member 906, shoulder 946 is spaced away or forms a gap with respect to the shoulder 942, thus forming the annular groove 322 (of FIG. 3). The distal cam member 902 further defines a central lumen 948. Partially visible within the central lumen 948 are the internal threads 950, which are discussed in more detail below with respect to the drive actuation assembly 308 (FIG. 3).

FIG. 9 further shows a fastener or screw 952. When the cam assembly 306 is fully assembled, the threads of the screw 952 telescope through the distal cam member 902, the medial cam member 906, the medial cam member 904, and the threads engage with the proximal cam member 900. That is, the head of the screw 952 abuts an internal shoulder (not visible) in the distal cam member 902, and the threads engage with the proximal cam member 900. The screw 952 provides a compressive force to hold the various members together to form the cam assembly 306.

Each of the cam members 900, 902, 904 and 906 may be individually created by injection molding using respective mold assemblies. In each case, the precision surfaces (e.g., the shoulders facing in respective and opposite directions parallel to the longitudinal central axis 914) may be formed directly by the mold assembly. Consider, as an example, the medial cam member 904. A two piece mode assembly may be used where the mold halves are brought together and separate by axial movement along the longitudinal central axis 914. In this way, shoulders (that eventually form annular grooves in the cam assembly) do not present undercuts in the direction of the travel or direction of separation of each mold half. Consider, as an example, shoulder 912 of the proximal cam member 900. As previously mentioned, the shoulder 912 (e.g., the distal face of the annular side wall 916) varies in axial position as a function of radial position around the longitudinal central axis 914. In the example system, a normal vector (e.g., vector perpendicular) at each incremental location along the distal face (e.g., incremental area in the limit as the area approaches zero) is parallel to the longitudinal central axis. Stated differently, in the example system the distal face defined by shoulder 912 is perpendicular to the outside diameter of the shoulder 912 all locations. The explanation is equally true for all the shoulders of the cam members, though in some cases the shoulders have proximal faces rather than distal faces.

Still referring to FIG. 9, the cam members of the example cam assembly 306 are shown with various indentations, troughs, and grooves. For example, cam member 904 has indentation 954 that is rectangular. Similarly, distal cam member 902 has an indentation 956 that has the shape of quadrilateral, and also has a series of troughs or grooves 958 that run parallel to the longitudinal central axis 914. The mold assembly for the distal cam member 902 may be a three piece mold—one mold assembly forming the shoulder 946 (and being separated along the longitudinal central axis 914 after curing) and two additional mold halves to form the distal region (including indentation 956), the two additional mold halves separate in opposite directions perpendicular to the longitudinal central axis 914. These indentations, troughs, and grooves are included to reduce the amount of material needed to fill the mold, to control cure time, and to address issues associated with differential expansion/contraction during the curing process, and thus may be omitted.

The example cam assembly 306 is designed and constructed for use with tube delivery systems having three moveable members in the shaft assembly, and thus three annular grooves in the cam assembly. However, if additional annular grooves are used, the additional annular grooves may be created by having additional cam members. For example, five separate cam members may be used to create a cam assembly with four annular grooves. Oppositely, if fewer annular grooves are used, fewer cam members may be needed. For example, three separate cam members may be used to create a cam assembly with two annular grooves.

Figure 10:
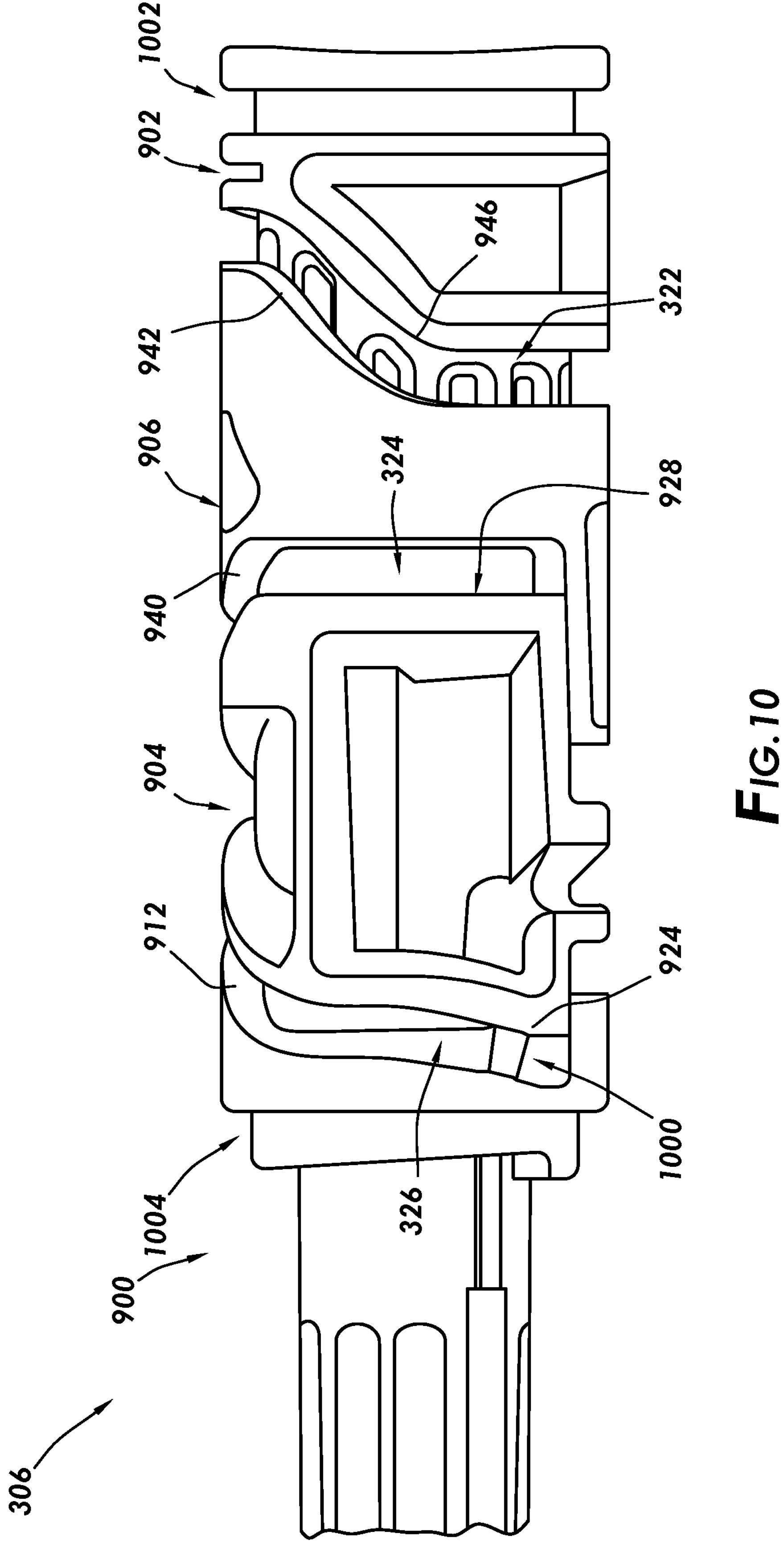
FIG. 10 shows a side elevation view of the cam assembly in an assembled form in accordance with at least some embodiments.

FIG. 10 shows a side elevation view of the cam assembly 306 in an assembled form. In particular, the cam assembly 306 is shown fully assembled, and the in the view of FIG. 10 the cam is rotated slightly from the rotational orientation of the view of FIG. 9. Visible in FIG. 10 is the proximal cam member 900 and distal cam member 902. Sandwiched between the proximal cam member 900 and the distal cam member 902 are medial cam member 904 and medial cam member 906.

FIG. 10 shows the shoulder 924 of the medial cam member 904. The shoulder 912 on the distal end of the proximal cam member 900 is in operational relationship with the shoulder 924 to form annular groove 326. In the example cam assembly 306, the floor or bottom of annular groove 326 is defined by an outside surface of the medial cam member 904. Location 1000 of the annular groove 326, and corresponding horizontal locations in annular grooves 324 and 322, represent the 360 degree rotational point in the rotation of the cam assembly 306 (see, e.g., FIG. 8).

FIG. 10 further shows the shoulder 940 of the medial cam member 906 on the proximal end of the medial cam member 904. The shoulder 940 is in operational relationship with the shoulder 928 (not visible) to form annular groove 324. In the example cam assembly 306, the floor or bottom of annular groove 324 is defined by an outside surface of the medial cam member 904. Similarly, shoulder 942 on the distal end of the medial cam member 904 is in operational relationship with the shoulder 946 to form annular groove 322. In the example cam assembly 306, the floor or bottom of annular groove 322 is defined by an outside surface of the distal cam member 902.

FIG. 10 also shows an annular groove 1002 defined on the distal end of the distal cam member 902. The annular groove 1002 forms a journal or bearing with a stationary component on an inside surface of the hand piece 102 (FIG. 1). Moreover, the side walls of the annular groove 1002 may also act as a thrust bearing during operation to hold the cam in place axially as forces are applied to the cam assembly 306 by way of the cam followers (not shown). The example cam assembly further defines an annular groove 1004 on the proximal end opposite the annular groove 1002. The annular groove 1004 also may act as journal bearing.

Figure 11:
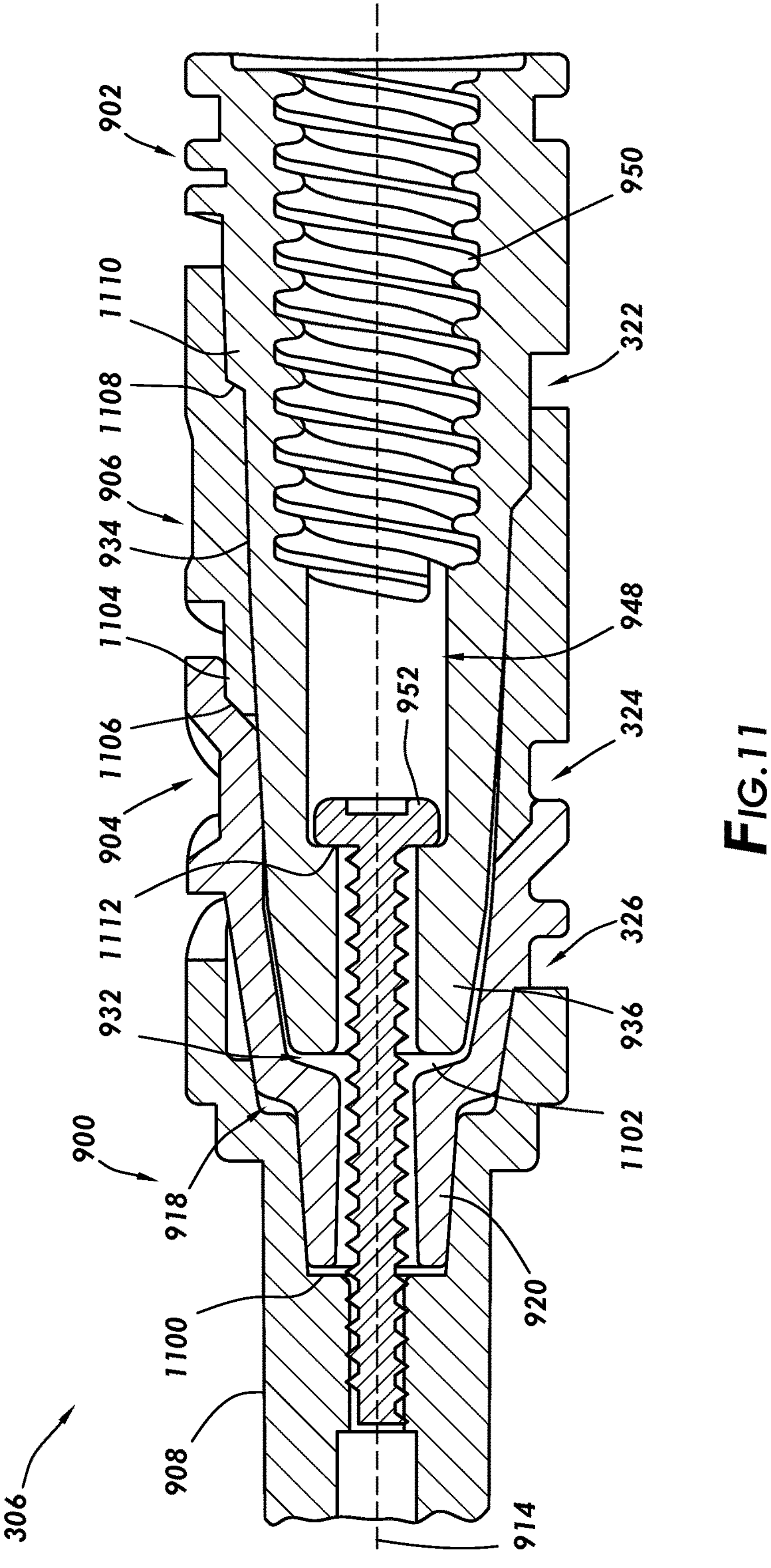
FIG. 11 shows a cross-sectional side-elevation view of the cam assembly in accordance with at least some embodiments.

FIG. 11 shows a cross-sectional, side-elevation view of the cam assembly 306 in accordance with at least some embodiments. In particular, FIG. 11 shows the proximal cam member 900 and distal cam member 902. Sandwiched between the proximal cam member 900 and the distal cam member 902 are medial cam member 904 and medial cam member 906. Further visible in FIG. 11 are the annular grooves 322, 324, and 326. Working from left to right, FIG. 11 shows spring support portion 908. Threads of the screw 952 engage within a bore inside the spring support portion 908, and thus the screw 952 provides a compressive force to hold the cam assembly 306 together.

The interior volume 918 of the proximal cam member 900 defines a counter bore 1100 into which the pin 920 of the medial cam member 904 is telescoped. In accordance with example embodiments, the inside diameter of the counter bore 1100 varies as function of axial location along the longitudinal central axis 914. In particular, the counter bore 1100 has a first inside diameter at the proximal-most location, a second inside diameter at a second location distal to the first location, and the second inside diameter is greater than the first inside diameter. In example embodiments, the change in inside diameter defines a frusto-conical shape and/or a parabolic shape widening distally.

Pin 920 defines an outside diameter that is complementary to the inside diameter of the counter bore 1100. In particular, the pin 920 has a first outside diameter at the proximal-most location, a second outside diameter at second location distal to the first location, and the second outside diameter is greater than the first outside diameter. In example embodiments, the change in outside diameter defines a frusto-conical shape and/or a parabolic shape widening distally. The tapers of the counter bore 1100 and the pin 920 enable the proximal cam member 900 and medial cam member 904 to self-align to be coaxial during assembly.

Still referring to FIG. 11, medial cam member 906 telescopes within and is concentrically arranged with medial cam member 904. Moreover, the distal cam member 902 telescopes through the medial cam member 906, and further telescopes within and is concentrically arranged with medial cam member 904. The example interior volume 932 of the medial cam member 904 defines a counter bore 1102 into which the pin 936 of the distal cam member 902 is telescoped. In accordance with example embodiments, the inside diameter of the counter bore 1102 varies as function of axial location along the longitudinal central axis 914. In particular, the counter bore 1102 has a first inside diameter at the proximal-most location, a second inside diameter at a second location distal to the first location, and the second inside diameter is greater than the first inside diameter. In example embodiments, the change in inside diameter of the counter bore 1102 defines a parabolic shape widening distally, but in other cases the shape may be frusto-conical or combinations of frusto-conical and parabolic widening distally.

Pin 936 defines an outside diameter that is complementary to the inside diameter of the counter bore 1102. In particular, the pin 920 has a first outside diameter at the proximal-most location, a second outside diameter at a second location distal to the first location, and the second outside diameter is greater than the first outside diameter. In the example embodiments, the change in outside diameter defines a parabolic shape widening distally, but in other cases the shape may be frusto-conical or combinations of frusto-conical shape and parabolic. The tapers of the counter bore 1102 and the pin 936 enable the medial cam member 904 and the distal cam member 902 to self-align to be coaxial during assembly.

The medial cam member 906 is telescoped over the pin 936. The central lumen 934 of the medial cam member 906 defines a shape complementary to the shape of the pin 936. In particular, central lumen has a first inside diameter at the proximal-most location, a second inside diameter at a second location distal to the first location, and the second outside diameter is greater than the first outside diameter. In the example embodiments, the change in inside diameter defines a parabolic shape widening distally, but in other cases the shape may be frusto-conical or combinations of frusto-conical shape and parabolic. The tapers of the pin 936 and the central lumen 934 enable the medial cam member 906 and the distal cam member 902 to self-align to be coaxial during assembly. Moreover, the medial cam member 906 defines an external annular shoulder 1104. The medial cam member 904 defines a complementary internal annular shoulder 1106. The external annular shoulder 1104 abuts the internal annular shoulder 1106 to control relative locations along the longitudinal central axis 914 of the medial cam members 904 and 906. In the example shown, the external annular shoulder 1104 defines a frusto-conical shape widening distally. Similarly, the internal annular shoulder 1106 defines a complementary frusto-conical shape widening distally, and thus the external annular shoulder 1104 and internal annular shoulder 1106 also assist to self-align to be coaxial during assembly. While the annular shoulders are illustratively shown as frusto-conical, in other cases the shape may be parabolic or combinations of parabolic and frusto-conical.

Still referring to FIG. 11, the medial cam member 906 also defines an internal annular shoulder 1108. The distal cam member 902 defines a complementary external annular shoulder 1110 on the outside surface of the pin 936. The internal annular shoulder 1108 abuts the external annular shoulder 1110 to control axial relationship of the medial cam member 906 relative to the distal cam member 902. In the example shown, the internal annular shoulder 1108 defines a frusto-conical shape widening distally. Similarly, the external annular shoulder 1110 defines a complementary frusto-conical shape widening distally, and thus the internal annular shoulder 1108 and external annular shoulder 1110 also to self-align to be coaxial during assembly. While the annular shoulders are illustratively shown as frusto-conical, in other cases the shape may be parabolic or combinations of parabolic and frusto-conical.

The central lumen 948 of the distal cam member 902 defines a counter bore 1112. The head of the screw 952 abuts the shoulder of the counter bore 1112 to apply compressive force to the overall cam assembly 306. In example embodiments, the distal cam member 902 also participates in the in the drive actuation. In particular, the inside diameter of the central lumen 948 includes internal threads 950. The internal threads work with a lead screw (discussed more below) to implement an example drive actuation assembly 308 (FIG. 3).

Returning briefly to FIG. 3. The specification now turns to a more detailed description of the drive actuation assembly 308. The drive actuation assembly 308 is designed and constructed to hold the cam assembly 306 against rotation unless and until a clinician presses pushbutton 108. Once released, the cam assembly 306 rotates to enable performing the myringotomy and placement of the tympanostomy tube.

Figure 12:
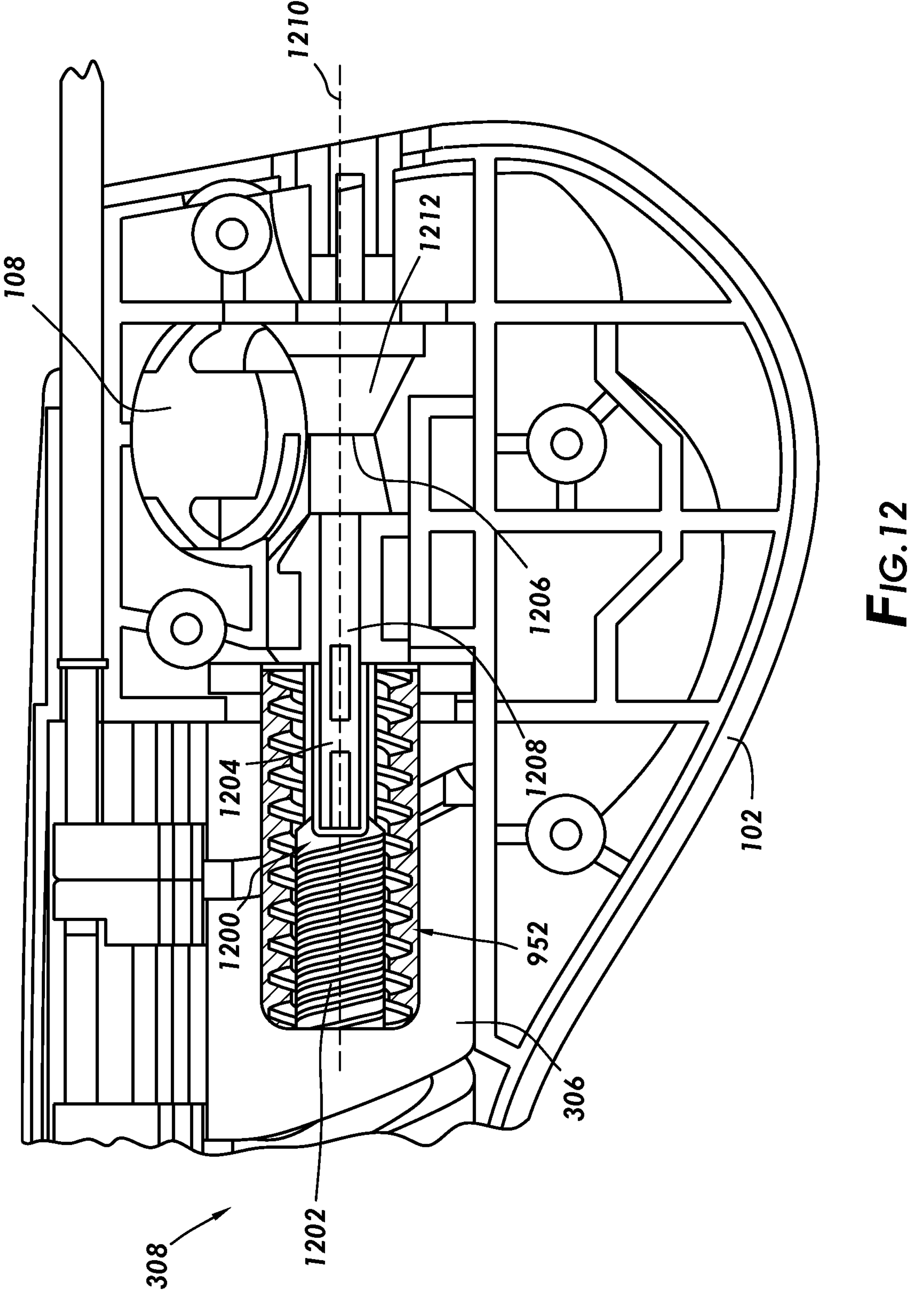
FIG. 12 shows, in greater detail, a side elevation view of an example tube delivery system with the portion of the hand piece removed in accordance with at least some embodiments.

FIG. 12 shows, in greater detail, a side elevation view of an example tube delivery system with the portion of the hand piece removed, and in accordance with at least some embodiments. In particular, visible in FIG. 12 are the cam assembly 306, a lead screw 1200, and the pushbutton 108. The cam assembly 306 is shown in partial cut away to reveal the internal threads 950. The lead screw 1200 defines a proximal end with external threads 1202 in operational relationship the internal threads 950 of the cam assembly 306. The lead screw 1200 further defines a shaft portion 1204 that extends distally, and a distal end of the shaft portion 1204 defines an actuation surface 1206.

In example embodiments, the lead screw 1200 is held against rotation by the shaft portion 1204. In particular, the example shaft portion 1204 defines an axial groove 1208. The axial groove 1208 defines a channel that is parallel to the longitudinal central axis 1210 of the lead screw 1200. The axial groove 1208, and in some cases a sibling axial groove on the opposite side of the lead screw 1200, interact with a stationary component of the hand piece 102 to hold the lead screw 1200 against rotation while enabling translation of the lead screw 1200 along the longitudinal central axis 1210 once the actuation surface 1206 is no longer held by the pushbutton 108.

The example pushbutton 108 further defines a complementary actuation surface 1212. In a non-triggered state prior to deployment, the actuation surface 1212 abuts the actuation surface 1206 of the lead screw 1200, thus holding the lead screw 1200 against translation along the longitudinal central axis 1210. In a triggered state of the drive actuation assembly 308, the actuation surface 1212 associated with the pushbutton 108 is moved clear of the actuation surface 1206 of the lead screw 1200. In particular, the clinician pushes or actuates the pushbutton 108. The force applied to the portion of the pushbutton 108 exposed through the hand piece 102 rotates the actuation surface 1212 out of alignment with the actuation surface 1206. In the view of FIG. 12, the rotation of the actuation surface 1212 moves the actuation surface 1212 toward the viewer of FIG. 12. Once the actuation surface 1212 is clear of the actuation surface 1206 of the lead screw 1200, the rotational force provided by the torsion spring 304 (FIG. 3) turns the cam assembly 306. Stated otherwise, in the non-triggered state prior to deployment the actuation surface 1212 abuts the actuation surface 1206 of the lead screw, which holds the lead screw 1200 against translation along the longitudinal central axis 1210 toward the distal end of the tube delivery system. Holding the lead screw 1200 against translation holds the cam 306 assembly against rotation. Once triggered, and the actuation surfaces are clear of each other, the cam assembly 306 is no longer held against rotation; it follows, the cam assembly 306 rotates under force provided by the torsion spring 304 and the rotation of the cam assembly 306 causes the lead screw 1200 to translate based on the interaction of the internal threads of the cam assembly and the external threads 1202 of the lead screw 1200.

The example actuation surface 1206 defines a distal face that resides in and/or defines a plane that is perpendicular to the plane of the page of FIG. 12. Similarly, the actuation surface 1212 defines a proximal face that resides in and/or defines a plane that is perpendicular to the plane of the page of FIG. 12, and also parallel to the plane defined by the actuation surface 1206. However, in yet still further embodiments the force used to actuate the pushbutton 108 can be controlled by having the actuation surface 1206 form an angle with respect to the longitudinal central axis 1210, and the actuation surface 1212 having a complementary angle. A bit more precisely, and considering the actuation surface 1206, a normal vector of the actuation surface 1206 may form an acute angle with the longitudinal central axis 1210 in a direction that creates a force tending to slide the actuation surface 1212 out of the abutting relationship. The actuation surface 1212 forms a complementary angle. Thus, the force tending to slide the actuation surface 1212 out of the abutting relationship reduces the amount of forced used on the pushbutton 108 to move the system to the triggered state. The precise angles and forces will depend on the materials from which the lead screw 1200 and pushbutton 108 are constructed, the coefficient of friction of the abutting surfaces, and a distance between the axis of rotation of the pushbutton 108 and the longitudinal central axis 1210.

Referring again to FIG. 3. The specification now turns to a more detailed description of the damper assembly 302. The damper assembly 302 is designed and constructed to limit or control the speed of rotation of the cam assembly 306 once the drive actuation assembly 308 releases the cam assembly 306 (e.g., is placed in a triggered state or condition). Consider, as an example, a tube delivery system 100 with the cam assembly 306 connected to the shaft assembly 104. Once the drive actuation assembly 308 is triggered, in the absence of the damper assembly 302 the torsion spring 304 may rotate the cam assembly 306 a complete revolution in 10-30 ms. However, for better operation of the tube delivery system 100, the complete revolution occurs in a time frame between 100 ms and 500 ms, inclusive. In one example case, the complete revolution occurs in a time frame of about 150 ms. Slowing the cam assembly 306 rotational speed, however, should not substantially limit the torque applied by the cam assembly 306 to the cam followers, so as not to limit the force applied to various moveable members of the shaft assembly during installation of a tympanostomy tube.

In order to control rotational speed of the cam assembly 306, example embodiments implement the damper assembly 302. The example damper assembly 302 is disposed within at the proximal end of the interior volume of the hand piece 102. The damper assembly 302 has a rotatable portion (discussed more below) that is coupled to the proximal end of the cam assembly 306, the rotatable portion turns with cam assembly 306 once released by the drive actuation assembly 308. Moreover, the damper assembly 302 has a stationary housing 328 that is held against rotation. The stationary housing 328 may define a tab or vane 330 that interacts with and/or abuts a feature of the interior volume of the hand piece 102 to hold the stationary housing 328 stationary while the cam assembly 306 is turning.

Figure 13A:
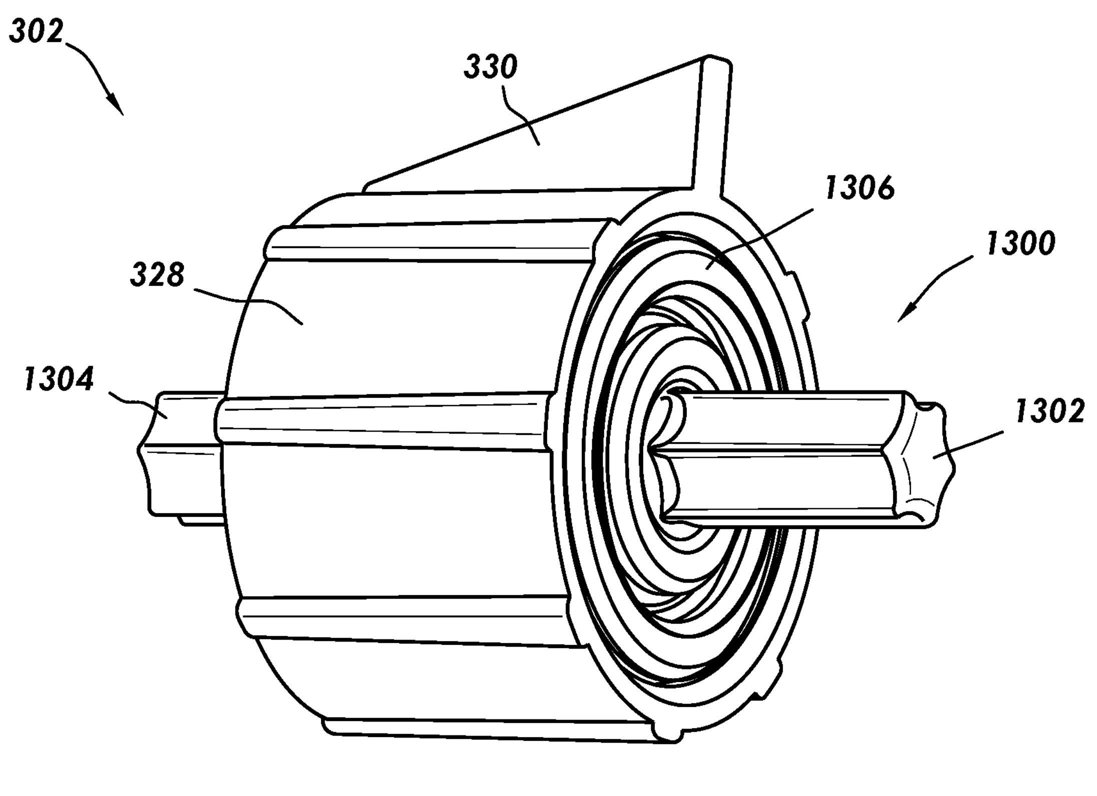
FIG. 13A shows a distal perspective side view of a damper assembly in accordance with at least some embodiments.

FIG. 13A shows a perspective side view of a damper assembly 302, looking from the distal side. In particular, visible in FIG. 13A is the stationary housing 328 including the vane 330. Also visible in FIG. 13A are portions of the rotor 1300, including a damping shaft or distal shaft 1302 and a winding shaft or proximal shaft 1304. As will be become clearer below, the rotor 1300 is telescoped within an annular channel defined within the stationary housing 328. In particular, in the example assembly the rotor 1300 is telescoped from the distal side toward the proximal side of the stationary housing 328 and thus into operational relationship with the stationary housing 328, and the rotor is held in place by seal ring 1306. The rotor 1300 turns with cam assembly 306 (FIG. 3) while the stationary housing 328 stays stationary.

Figure 13B:
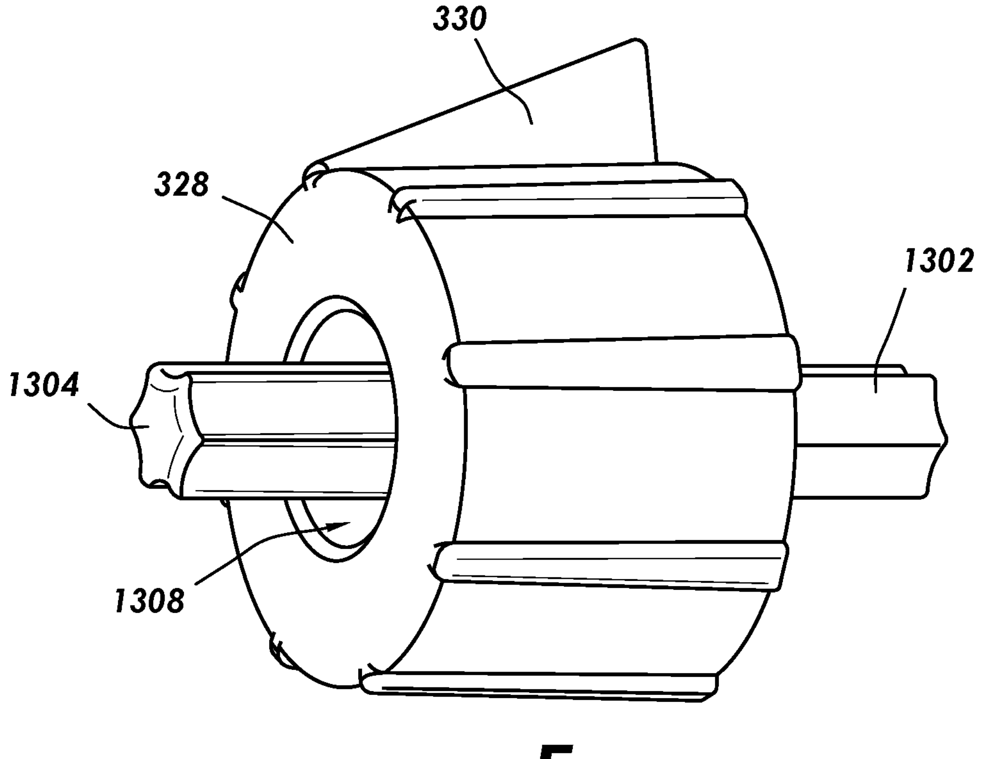
FIG. 13B shows a proximal perspective side view of a damper assembly in accordance with at least some embodiments.

FIG. 13B shows a proximal perspective side view of the damper assembly 302. In particular, visible in FIG. 13B is the stationary housing 328 including the vane 330. Better visible in FIG. 13B is the proximal shaft 1304 extending proximally from the stationary housing 328. In particular, the stationary housing 328 defines an internal annular channel (not visible), and an interior wall of the annular channel defines a bore 1308 on the proximal side of the stationary housing 328. The proximal shaft 1304 telescopes through and is concentrically arranged with the bore 1308. The optional proximal shaft 1304 may be used during assembly of a tube delivery system 100 (FIG. 1) to wind the torsion spring 304 (also FIG. 1). Other winding techniques are possible, and thus the proximal shaft 1304 may be omitted, or replaced with a socket arrangement for winding.

Figure 14:
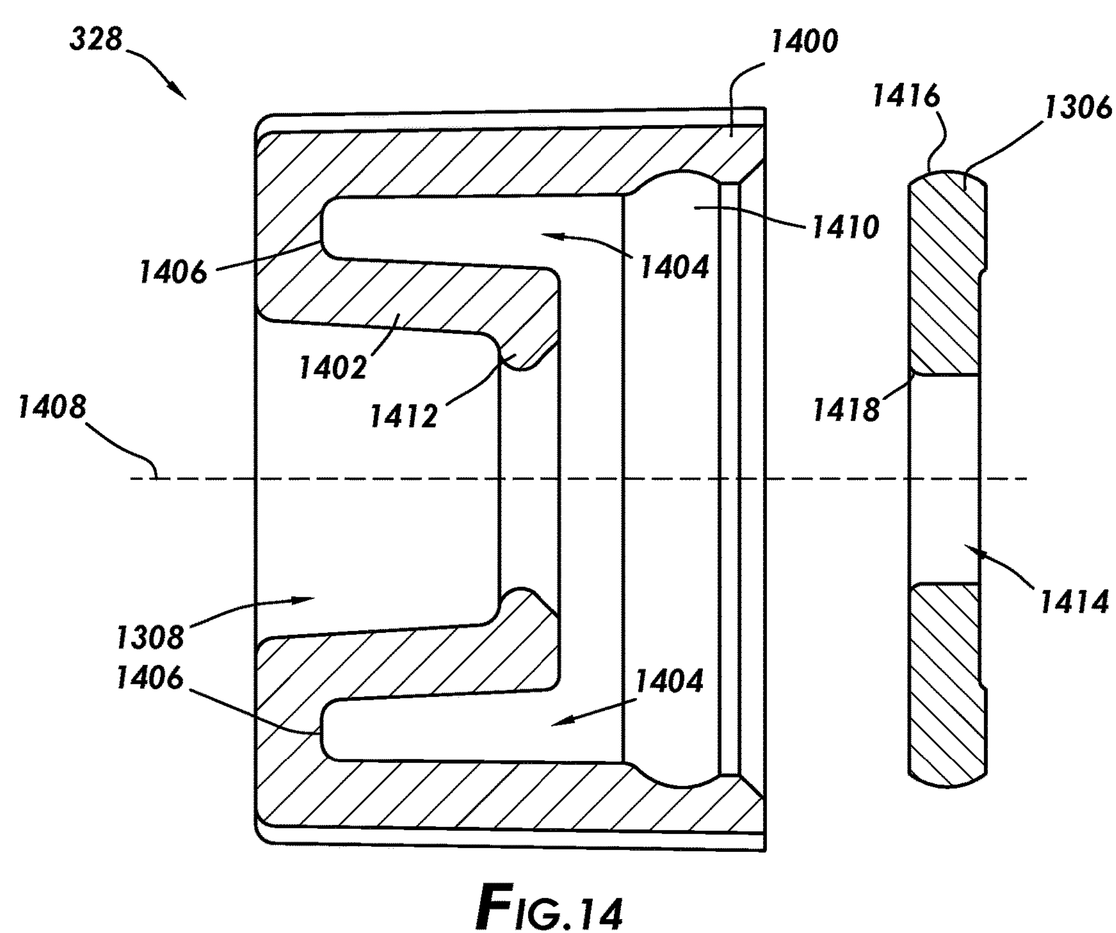
FIG. 14 shows a cross-sectional side view of the stationary housing of the damper assembly in accordance with at least some embodiments.

FIG. 14 shows a cross-sectional side view of the stationary housing of the damper assembly, along with a cross-sectional side view of the seal ring. In particular, FIG. 14 shows that the example stationary housing 328 defines an external wall 1400. The external wall 1400 thus defines a circular outside diameter of the stationary housing 328. The example stationary housing 328 also defines an internal wall 1402 concentrically arranged with the external wall 1400. The internal wall 1402 has an inside surface that defines the bore 1308. An inside diameter or inside surface of the external wall 1400 and an outside diameter or outside surface of the internal wall 1402 define an annular channel 1404. The annular channel 1404 defines an open top (e.g., open to the distal side of the stationary housing 328). The annular channel 1404 also defines a closed bottom 1406. The example annular channel 1404 circumscribes the longitudinal central axis 1408 of the stationary housing 328.

The example stationary housing also includes an annular channel 1410 defined on an inside diameter of the external wall 1400 of the stationary housing 328. The seal ring 1306 snaps into the annular channel 1410 during assembly. The seal ring 1306, when snapped in place, not only seals and holds a viscous fluid within the internal volume of the stationary housing 328, but also holds the rotor 1300 (FIG. 13) in place within the stationary housing 328. The example stationary housing 328, and particular the internal wall 1402, further defines an annular ring or annular ridge 1412 disposed on the distal end of the internal wall 1402, and the annular ridge 1412 projecting toward the longitudinal central axis 1408. The annular ridge 1412 works in conjunction with the rotor 1300 to seal the viscous fluid within the internal volume of the stationary housing 328.

FIG. 14 further shows a cross-sectional view of the seal ring 1306. In particular, the example seal ring 1306 defines an annular disk or annular ring with a central aperture 1414. The outside diameter of the seal ring 1306 defines an annular seal or annular ridge 1416 designed and constructed to mate with and snap into the annular channel 1410 of the stationary housing 328. The example central aperture 1414 defines a chamfer 1418 on the proximal side of the central aperture 1414. The chamfer 1418 may assist in centering the rotor 1300 (FIG. 13) as well assist in sealing against rotor 1300 to prevent leakage viscous fluid.

Figure 15:
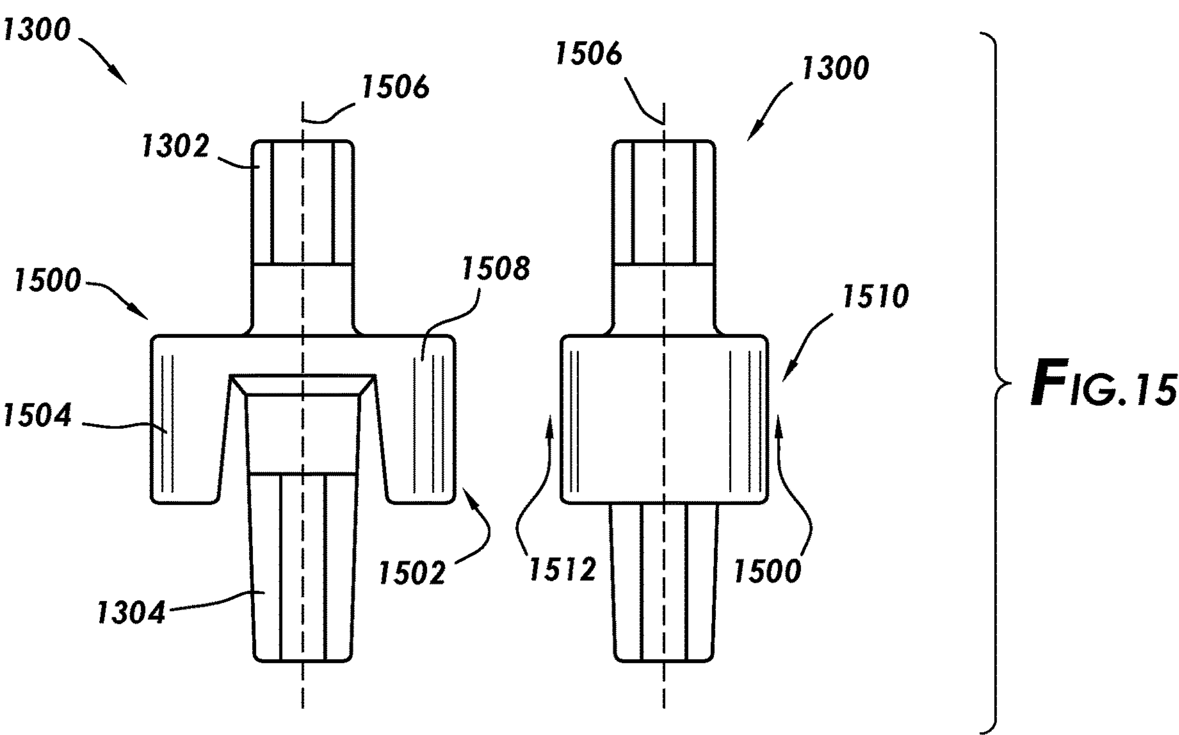
FIG. 15 shows side elevations views of the rotor in accordance with at least some embodiments.

FIG. 15 shows two side-elevation views of the rotor 1300. In particular, and referring to view on the left, the example rotor 1300 includes the distal shaft 1302 and the proximal shaft 1304. Disposed between the distal shaft 1302 and the proximal shaft 1304 is a set of walls or arcuate vanes, comprising arcuate vane 1500 and arcuate vane 1502. The arcuate vanes are rigidly coupled to the distal shaft 1302 and proximal shaft 1304. The arcuate vane 1500 defines an outside surface 1504 and an inside surface (not visible). The outside surface 1504 and the inside surface are designed and constructed to telescope within the annular channel 1404 (FIG. 14). Stated differently, the arcuate vane 1500 may be considered a wall extending proximally with a curvature designed and constructed to telescope with the annular channel 1404. Similarly, the arcuate vane 1502 defines an outside surface 1508 and an inside surface (not visible). The outside surface 1508 and inside surface of arcuate vane 1502 are designed and constructed to telescope within the annular channel 1404. Stated differently, the arcuate vane 1502 may be considered a wall extending proximally with a curvature designed and constructed to telescope with the annular channel 1404. In accordance with example embodiments, the arcuate vanes 1500 and 1502 are mirror images of each other across the longitudinal central axis 1506.

Referring to the view on the right of FIG. 15, the view on the right again shows the example rotor 1300, but the rotor 1300 is turned 45 angular degrees about the longitudinal central axis 1506. Thus, visible in the right view of FIG. 15 is the arcuate vane 1500. The right view of FIG. 15 shows that the arcuate vanes 1500 and 1502 span less than 360 angular degrees around the longitudinal central axis 1506, and thus form gap regions 1510 and 1512 on opposite sides of the rotor 1300. The arcuate length of the gap regions may be designed and constructed, in combination with other features, to control the rotational speed enabled by the damper assembly 302.

Referring simultaneously to FIGS. 14 and 15. Assembly of the damper assembly 302 may involve putting a predetermined volume of damping grease (e.g., special purpose viscous damping grease, or vacuum grease) in the annular channel 1404 formed by the stationary housing 328. Thereafter, the rotor 1300 is telescoped along the longitudinal central axis 1408 such that the longitudinal central axis 1408 and the longitudinal central axis 1506 are coaxial, and such that the rotor 1300 and stationary housing 328 are concentrically arranged. Alternatively, the rotor 1300 may be telescoped together with the stationary housing 328, and thereafter the predetermined volume of damping grease is applied (e.g., half in the first gap region between the annular vanes, and the second half in the second gap region between the annular vanes). Regardless of the precise order, when fully engaged the proximal shaft 1304 extends into the bore 1308. In some cases, and as shown, the proximal shaft 1304 may extend beyond the stationary housing 328 in the proximal direction. Thereafter, the seal ring 1306 is telescoped over the distal shaft 1302 and snapped into place within the annular channel 1310.

The example damper assembly 302 thus defines a plurality of shear volumes or shear regions, with each shear region defined between a surface of an arcuate vane and an internal surface of the annular channel 1404 (e.g., the inside diameter of the external wall 1400, and the outside diameter of the internal wall 1402). Consider, as an example, arcuate vane 1500. Arcuate vane 1500 defines the outside surface 1504 and corresponding inside surface (not visible). The outside surface 1504 is in operational relationship, but not touching, the inside diameter of the external wall 1400. The inside area of the arcuate vane 1500 is in operational relationship, but not touching the outside diameter of the internal wall 1402.

In accordance with example systems, the offset or spacing (measured perpendicularly to the longitudinal central axis 1506) between the outside surfaces of the arcuate vanes 1500 and 1502 and an inside diameter of the external wall 1400 of the annular channel 1404 is about 0.0040 inch (about 0.102 mm). Similarly, the offset or spacing (again measured perpendicularly to the longitudinal central axis 1506) between the inside surfaces of the arcuate vanes 1500 and 1502 and an outside diameter of the inner wall 1402 of the annular channel 1404 is about 0.0040 inch (about 0.102 mm). While the offsets are the same in the example embodiment, such need not be the case. Moreover, the offset may change based on viscosity of the viscous fluid within the damper, total surface of area (both inside and outside) of the arcuate surfaces, volume of the annular channel 1404 within the gap regions 1510 and 1512 between within the annular channel 1404 between the arcuate vanes 1500 and 1502, desired rotational speed, and the like.

The damper assembly 302 is thus designed and constructed to limit or control the speed of rotation of the cam assembly 306 once the drive actuation assembly 308 releases the cam assembly (e.g., is placed in a triggered state or condition). The vane length and surface area of the arcuate vanes, the offset between the vanes and the stationary portions of the annular channel 1404, the volume of the annular channel in the gap regions between the vanes, and the viscosity of the viscous fluid, are designed and selected to enable a full 360 angular degrees of rotation of the cam assembly to occur in a time frame between 100 ms and 500 ms, inclusive, without limiting, or without significantly limiting, the torque the torsion spring applies the cam assembly. In one example embodiment, the vanes take up about 80% of the volume within the damper assembly, and thus the gap space represents about 20% of the volume of the annular channel.

Returning to FIG. 3. In the various embodiments discussed to this point the drive actuation mechanism 308 is implemented as a lead screw that interacts with internal threads of the cam assembly 306. However, other drive actuation mechanisms are possible, including drive actuation mechanisms that do not utilize internal threads of the cam assembly 306.

Figure 16:
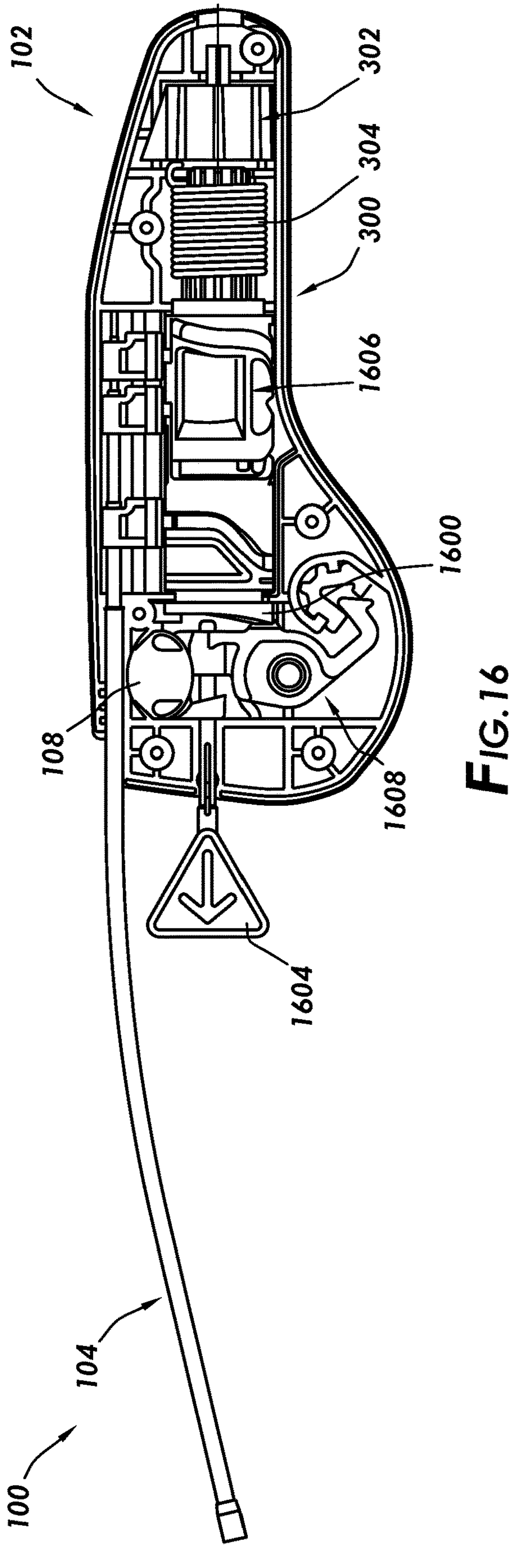
FIG. 16 shows a side elevation view of an example tube delivery system with a portion of the hand piece removed to show various components of the drive assembly, and in accordance with at least some embodiments.
Figure 17:
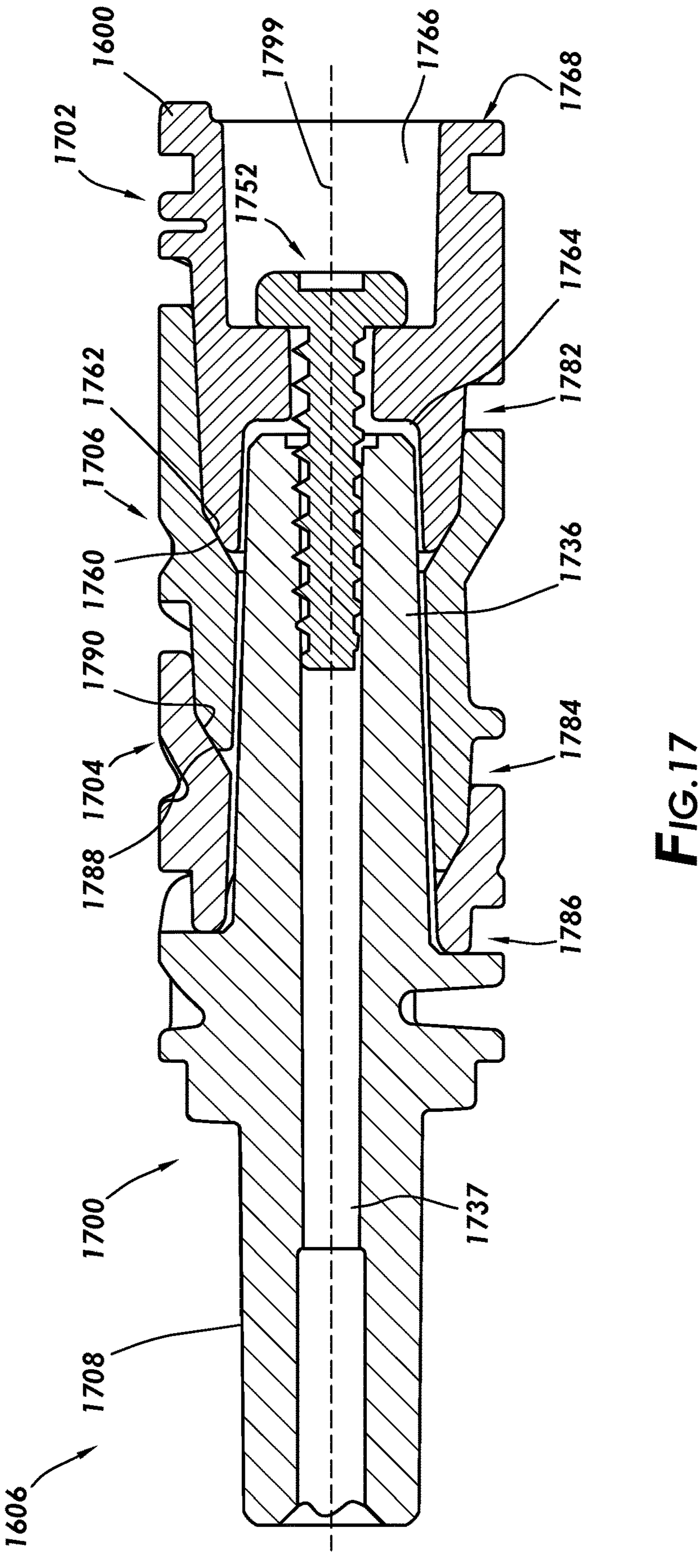
FIG. 17 shows a cross-sectional side-elevation view of the cam assembly in accordance with at least some embodiments.

FIG. 16 shows a side elevation view of another example tube delivery system 100 with a portion of the hand piece removed to show an alternative drive actuation mechanism. In particular, FIG. 17 shows the example tube delivery system 100 comprises the hand piece 102 and the shaft assembly 104. Disposed within the hand piece 102 is the proximal end of the shaft assembly 104, along with various components of the drive assembly 300. The example drive assembly 300 comprises, working from right to left in the figure, the damper assembly 302, the torsion spring 304, an alternative cam assembly 1606, and an alternative drive actuation mechanism 1608 (that includes the push pushbutton 108). The shaft assembly 104, the damper assembly 302, and the torsion spring 304 may be identical to the components discussed above, and thus are not described again here so as not to unduly lengthen the specification. The alternative drive actuation mechanism 1600 changes slightly the cam assembly, and thus the specification first turns to the modifications to the cam assembly 1606.

The example cam assembly 1606 of FIG. 16, from the standpoint of the layout of the annular grooves, and how those grooves interact with the cam followers, is identical to the previous cam assembly 306 (FIG. 3). From an exterior appearance standpoint, one change from the prior embodiments is the presents of a tab or boss 1600 on the distal end of the cam assembly 306 and disposed at the outer boundary. The boss 1600, in combination with the example drive actuation mechanism 1608, holds the cam assembly 1606 against rotational until the locking mechanism 1604 is removed and the pushbutton 108 is pressed or activated. Indeed, the cam assembly 1606 may be constructed from the individual cam members as previously discussed, though the cam assembly 1606 need not define the internal threads 950 (FIG. 9) since those internal threads are not needed in the presence of the drive actuation mechanism 1608. Nevertheless, in the absence of the need for the internal threads, the various cam members that are assembled together to of the cam assembly 1606 may be arranged differently than for cam assembly 306.

FIG. 17 shows a cross-sectional, side-elevation view of the example cam assembly 1606. In particular, FIG. 17 shows a proximal cam member 1700 and a distal cam member 1702. Sandwiched between the proximal cam member 1700 and the distal cam member 1702 are a medial cam member 1704 and a medial cam member 1706. Further, visible in FIG. 17 are annular grooves 1782, 1784, and 1786, which correspond directly to annular grooves 322, 324, and 326 (FIG. 3), respectively. The various shoulders of the cam members that create the annular grooves are positioned the same as with respect to cam assembly 306, and thus the various components of the annular grooves 1782, 1784, and 1786 are not described again in detail so as not to unduly lengthen the specification.

The example proximal cam member 1700 defines a spring support portion 1708 and a medial portion. Opposite the spring support portion 1708 the proximal cam member 1700 defines pin 1736. A through bore 1737 extends the length of the proximal cam member 1700 along the longitudinal central axis 1799. Threads of the screw 1752 engage within a through bore 1737, and thus the screw 1752 provides a compressive force to hold the cam assembly 1606 together. The medial cam member 1704, the medial cam member 1706, and the distal cam member 1702 each are telescoped over and concentrically arranged with the pin 1736. In the example shown, the pin 1736 has a first outside diameter at the proximal-most location, a second outside diameter at a second location distal to the first location, and the second outside diameter is smaller than the first outside diameter. That is, in example cases the pin 1736 forms a frusto-conical shape and/or a parabolic shape narrowing distally. The frusto-conical shape may help concentrically align the various cam members during assembly.

Medial cam member 1704 telescopes over the pin 1736 and abuts a medial portion of the proximal cam member 1700. The medial cam member 1704 thus defines a through bore telescoped over the pin 1736, as well as an internal shoulder 1788. In accordance with example embodiments, the internal shoulder 1788 varies in position as a function of axial location along the longitudinal central axis 1799. In particular, the internal shoulder 1788 is a spiral-shaped internal shoulder 1788 that is parallel to the annular groove 1784.

Medial cam member 1706 telescopes over the pin 1736, and also telescopes within and is concentrically arranged with medial cam member 1704. In particular, the medial cam member 1707 defines a pin or plug portion having a through bore, as well as an external shoulder 1790. When assembled, the external shoulder 1790 abuts the internal shoulder 1788 of the medial cam member 1704. Thus, the combination of the frusto-conical shape of the pin 1736 and the mating shoulders 1788 and 1790 may work to concentrically arrange the components during assembly. The medial cam member 1706 further defines a counter bore that defines internal shoulder 1760.

Distal cam member 1702 telescopes over the pin 1736, and also telescopes within and is concentrically arranged with medial cam member 1706. In particular, the distal cam member 1702 defines a pin or plug portion having a through bore, as well as an external shoulder 1762. When the pin portion of the distal cam member 1702 telescopes within the through bore of the medial cam member 1706, the internal shoulder 1760 of the medial cam member 1704 abuts the external shoulder 1762 of the distal cam member 1702. Moreover, in the example system the distal cam member 1702 defines a counter bore 1764 that telescopes over the distal end of the pin 1736. Thus, the combination of the frusto-conical shape of the pin 1736 and the mating shoulders 1760 and 1762 may work to concentrically arrange the components during assembly. The distal cam member 1702 further defines a second counter bore 1766. The head of the screw 1752 telescopes within and abuts the shoulder created by the counter bore 1766 to apply compressive force to the overall cam assembly 1706.

In example embodiments, the distal cam member 1702 also participates in the in the drive actuation. In particular, the distal face 1768 of the distal cam member 1702 defines a protruding tab or boss 1600. The example boss 1600 protrudes distally, parallel to the longitudinal central axis 1799. Moreover, the boss 1600 is defined at the outer periphery of the distal cam member 1702. Stated differently, the distal face 1768 defines a plane that is perpendicular to the longitudinal central axis 1799. The boss 1600 extends distally beyond the plane in a direction parallel to the longitudinal central axis 1799. The boss 1600 works with a crowbar (discussed more below) to hold the cam assembly 1606 in a non-triggered state prior to deployment, with the with the torsion spring wound. The specification thus turns to the example actuation mechanism.

Figure 18:
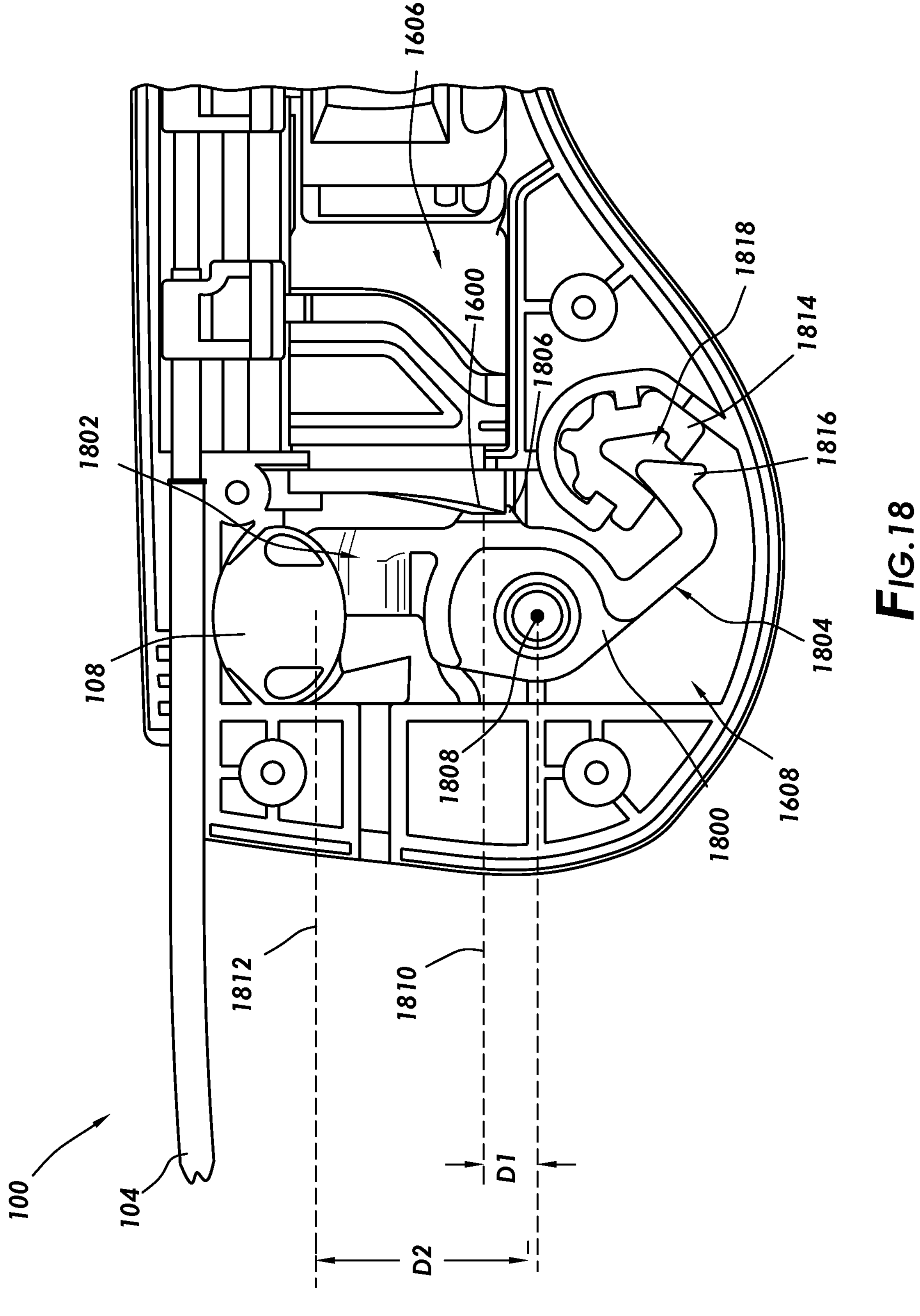
FIG. 18 shows, in greater detail, a side elevation view of an example tube delivery system with the portion of the hand piece removed in accordance with at least some embodiments.

FIG. 18 shows, in greater detail, a side elevation view of an example tube delivery system with the alternative drive actuation mechanism. In particular, FIG. 18 shows a portion of the cam assembly 1606 and the drive actuation mechanism 1608. However, the locking mechanism 1604 shown in FIG. 16 is removed in the view of FIG. 18. The drive actuation mechanism 1608 comprises an actuator or crowbar 1800. The crowbar 1800 includes a locking portion 1802, a catch portion 1804, and a wedge or boss 1806. The crowbar 1800 defines an axis of rotation 1808. In the view of FIG. 18 the axis of rotation is perpendicular to the plane of the page, and thus the axis of rotation 1808 is shown as a dot.

In the latched configuration of the drive actuation mechanism shown in FIG. 18, the boss 1806 of the crowbar 1800 contacts or abuts the boss 1600 defined at the distal end of the cam assembly 1606. Thus, the boss 1806 of the crowbar 1800 holds the cam assembly 1606 against rotation. In some cases the interaction surfaces between the boss 1806 and the boss 1600 may form a plane parallel to the plane of the page in FIG. 18. However, in other cases, and to reduce the button force used to actuate the system, the example boss 1806 defines an interaction surface that is sloped or wedge shaped. The boss 1600 likewise forms an interaction surface that is sloped or wedge shaped in a complementary direction, and the interaction surfaces together create a force tending to rotate the crowbar 1800 counter-clockwise in view of FIG. 18. Stated otherwise, the interaction surfaces are designed and constructed to create a force tending to disengage the bosses 1806 and 1600; however, the pushbutton 108 blocks such movement until pressed.

In particular, the pushbutton 108 defines an actuation surface (not visible) that holds the crowbar 1800 against counter-clockwise rotation in the view of FIG. 18. Similarly, the locking portion 1802 of the crowbar 1800 defines an actuation surface that is complementary to the actuation surface on the pushbutton 108. In the non-triggered state prior to deployment shown in FIG. 18, the actuation surfaces interact or abut, and create a force tending to rotate the crowbar 1800 in the clockwise direction in the view of FIG. 18. In other words, the pushbutton 108 holds the crowbar 1800 against rotation in the non-triggered state prior to deployment.

One design element that is of concern is the amount of force used to move the pushbutton 108 and thus trigger the tube delivery system. A force that is too high may result in inadvertent movement of the distal end of the shaft assembly 104, which may result in an improper placement of the tympanostomy tube. A force that is too low may result in premature triggering of the tube delivery system 100. In example cases, a pushbutton force of about two newtons is desirable. In order to achieve the example pushbutton force, the designer of the system may control the slope of the interaction surfaces of the bosses 1806 and 1600, may control the slope of the actuation surfaces of the pushbutton 108 and the locking portion 1802, and may control the relative distances of the interaction and contact surfaces from the axis of rotation 1808. For example, the interaction surfaces of the bosses 1806 and 1600 may two resultant forces: one force perpendicular to the plane of the page, and another force parallel to the plane of the page along line 1810. Similarly, the actuation surfaces as between the pushbutton 108 and the locking portion 1802 may have two resultant forces: one force perpendicular to the plane of the page, and another force parallel to the plane of the page along line 1812. Note that the force associated with the line 1812 is in the opposite direction to the force associated with line 1810.

The force along line 1810 creates torque based on the distance D1, measured perpendicularly to the axis of rotation 1808. The force along line 1812 creates a torque based on the distance D2, again measured perpendicularly to the axis of rotation 1808. Given that D2 is greater than D1, it follows that the force at the actuation surfaces between the pushbutton 1008 and locking portion 1802 is proportionally lower to hold the crowbar 1800 against rotation, thus lowering the pushbutton forced used for triggering or actuation. In at least some cases the distance D2 is at least twice the distance D1, and in other cases the distance D2 is at least four times distance D1. The specification now turns to sound or noise considerations.

As mentioned above, any mechanical vibration or mechanical sound created within the tube delivery system 100 is transferred directly to the tympanic membrane. Thus, the mechanical sound will be perceived as a loud noise or sound by the patient. The inventors of the present application have found that one source mechanical sound that causes issues with related-art devices may be the drive actuation mechanism. In particular, in related-art devices, once the tube delivery device is triggered actuated, the mechanical structure or linkages of the drive actuation mechanism produce sound. For example, the mechanical structure may, based on the forces, contact the stationary components within the handle, causing mechanical sound. In other cases, once released or triggered the drive actuation mechanism may fall under force of gravity and rattle around with the handle.

The drive actuation mechanism 1608 addresses these issues, at least in part, by capturing the crowbar 1800 after actuation. More particularly, after the cam assembly 1606 is released, the example embodiments capture or latch the crowbar 1800 into a latched configuration which prevents both over rotation and reverse rotation of the crowbar 1800. The capturing or latching may take any suitable form, but in the example embodiments the latching is accomplished by the catch portion 1804 interacting with a stationary latch or soft stop 1814. In particular, in the example embodiment the crowbar 1800 defines the catch portion 1804 on the opposite side of the axis of rotation 1808 from the locking portion 1802. The example catch portion 1804 defines a barb 1816 on a distal end thereof. In the non-triggered state of the drive actuation assembly 1608 shown in FIG. 18, the barb 1816 resides (at least partially) outside the soft stop 1814.

The soft stop 1814 may take any suitable form. For example, the soft stop 1814 may be an elastomeric component comprising a mating feature that is complementary to the barb 1816. In the example case shown, the mating feature 1818 is a barb-shaped recess defined on an outer surface of the soft stop 1814. However, depending on the hardness of the soft stop 1814, the mating feature 1818 may take any suitable form. For example, the mating feature may be channel that runs fully or partially across the soft stop 1814. The mating feature may be a blind bore or a counterbore defined within the material of the soft stop 1814 and into which the catch portion 1804, such as the barb 1816, is inserted. In yet still further cases, the mating feature may be film or membrane that is punctured by the catch portion 1804, such as by the barb 1816. Regardless of the precise design, the soft stop 1814 is designed and constructed to enable partial rotation of the crowbar 1800 in a first direction, but then to capture and hold the crowbar 1800 against further rotation in the first direction and hold the crowbar 1800 against rotation in a second direction, opposite the first direction. That is, once captured the crowbar 1800 cannot rotate in either direction. In example cases, the soft stop 1814 is made of an elastomeric material having a Shore A hardness of between and including 50 and 85, and in one particular example a Shore A hardness of about 70. The soft stop 1814 may be held in place within the handle in any suitable form, such as being held in place by a set of stationary internal walls of the handle as shown in FIG. 18.

Figure 19:
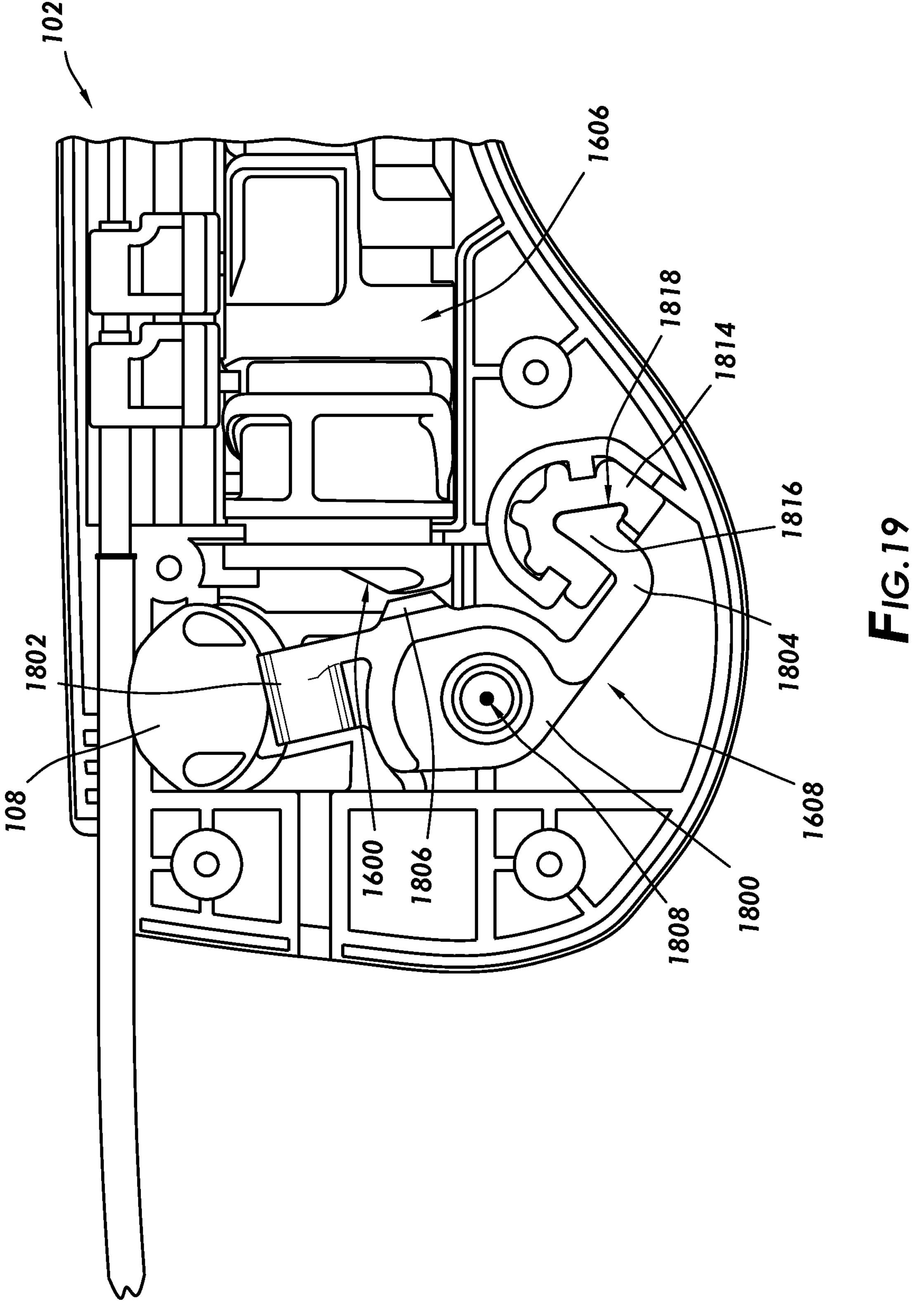
FIG. 19 shows, in greater detail, a side elevation view of an example tube delivery system with the portion of the hand piece removed in accordance with at least some embodiments.

FIG. 19 shows a side elevation view with the drive actuation mechanism 1608 in a triggered condition or triggered state. In particular, FIG. 19 shows the crowbar 1800 of the drive actuation mechanism 1608 rotated about the axis of rotation 1808 and captured the soft stop 1814. That is, between the non-triggered state prior to deployment as shown in FIG. 18, and the triggered state shown in FIG. 19, the clinician has pressed the pushbutton 108. Pressing the pushbutton 108 moves the actuation surface of the pushbutton 108 clear the actuation surface of the locking portion 1802. With actuation surfaces clear of each other, the force imparted to the crowbar 1800 by the interaction between the boss 1806 and the boss 1600 rotated the crowbar 1800 in the counter-clockwise direction around the axis of rotation 1808. Once the bosses 1806 and 1600 were clear of each other, the cam assembly 1606 rotated about its rotational axis.

As the crowbar 1800 rotated counter-clockwise the catch portion 1804, and in particular the barb 1816, telescoped within or mated with the mating surface 1818 of the soft stop 1814. In interacting with the soft stop 1814, further counter-clockwise rotation of the crowbar 1800 was blocked such that the locking portion 1802 did not over-rotate to hit the locking feature of the pushbutton 108 or any other interior feature of the handle 102. Moreover, in interacting with the soft stop 1814, the crowbar 1800 was prevented from bouncing back or reverse-rotation (e.g., clockwise in the view of FIG. 19). In that way, the crowbar 1800 does not create mechanical sound by hitting the cam assembly 1606. Thus, with the respect to actuation of the drive actuation mechanism 1608, the mechanical sound creation may be limited to the pushbutton 108 hitting a travel stop, and the slight mechanical sound of the example barb 1816 moving the through and into the channel of the mating feature 1818 the soft stop 1814.

Figure 20:
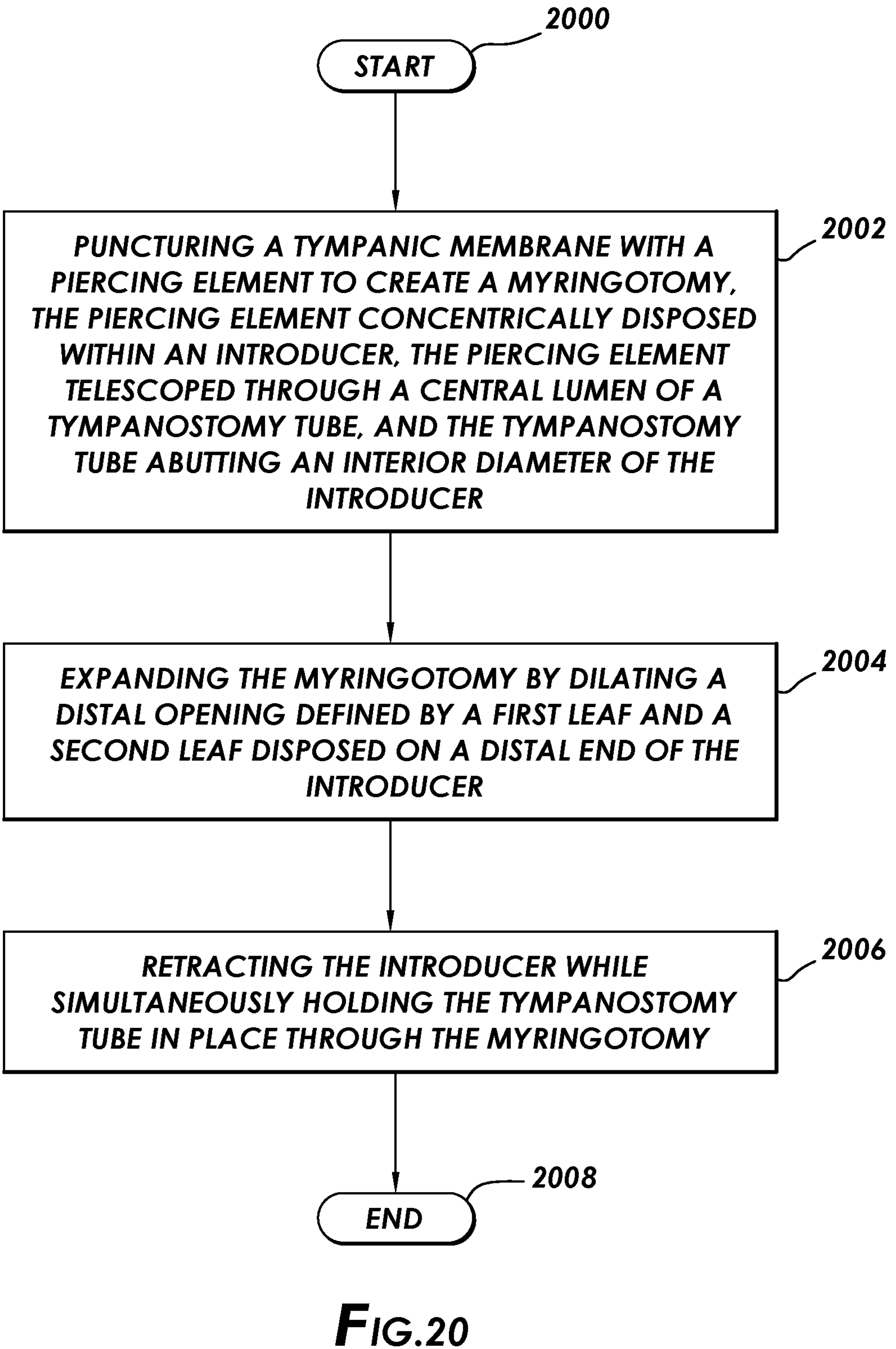
FIG. 20 shows a method accordance with at least some embodiments.

FIG. 20 shows a method accordance with at least some embodiments. In particular, the method starts (block 2000) and comprises: puncturing a tympanic membrane with a piercing element to create a myringotomy, the piercing element concentrically disposed within an introducer, the piercing element telescoped through a central lumen of a tympanostomy tube, and the tympanostomy tube abutting an interior diameter of the introducer (block 2002); expanding the myringotomy by dilating a distal opening defined by a first leaf and a second leaf disposed on a distal end of the introducer (block 2004); retracting the introducer while simultaneously holding the tympanostomy tube in place through the myringotomy (block 2006). Thereafter the methods ends (block 2008), likely to be repeated in the second ear of the patient.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A tube delivery system for installing a tympanostomy tube, the tube delivery system comprising:

a hand piece;

a shaft assembly extending distally from the hand piece, the shaft assembly comprising:

an elongate outer tube;

an introducer defining a distal end, a first leaf on the distal end, a second leaf on the distal end, and an inside diameter, the introducer concentrically disposed within the elongate outer tube;

the tympanostomy tube, wherein the tympanostomy tube is disposed within and directly abuts the inside diameter of the introducer; and a pusher concentrically disposed within the introducer; and a drive assembly disposed within the hand piece, the drive assembly configured to longitudinally translate the introducer and the pusher relative to the elongate outer tube, wherein the drive assembly is configured to dilate the first leaf and the second leaf by the pusher distally translating the tympanostomy tube relative to the introducer such that the tympanostomy tube directly contacts and dilates the first leaf and the second leaf to facilitate installation of the tympanostomy tube.

2. The tube delivery system of claim 1 wherein the introducer further comprises:

a first longitudinal kerf on a first side of the introducer between the first leaf and the second leaf; and a second longitudinal kerf, the second longitudinal kerf on a second side between the first leaf and the second leaf.

3. The tube delivery system of claim 2 wherein the first longitudinal kerf and the second longitudinal kerf are coplanar with a longitudinal central axis of the introducer.

4. The tube delivery system of claim 1 further comprising:

a first longitudinal kerf on a first side of the introducer between the first leaf and the second leaf;

a first circumferential kerf that intersects a proximal end of the first longitudinal kerf;

a second longitudinal kerf on a second side of the introducer between the first leaf and the second leaf; and a second circumferential kerf that intersects a proximal end of the second longitudinal kerf.

5. The tube delivery system of claim 4 further comprising the first circumferential kerf and the second circumferential kerf are coplanar, and a plane defined by the first and second circumferential kerfs is perpendicular to a longitudinal central axis of the introducer at the distal end of the introducer.

6. The tube delivery system of claim 4 further comprising:

a first strain relief aperture at a first end of the first circumferential kerf;

a second strain relief aperture at a second end of the first circumferential kerf;

a third strain relief aperture at a first end of the second circumferential kerf; and a fourth second strain relief aperture at a second end of the second circumferential kerf.

7. The tube delivery system of claim 1 wherein the shaft assembly further comprises:

a proximal portion defining a proximal longitudinal axis;

a distal portion defining a distal longitudinal axis; and a bend between the proximal portion and the distal portion;

wherein an obtuse angle between the proximal longitudinal axis and the distal longitudinal axis is between and including 170 angular degrees and 160 angular degrees.

8. The tube delivery system of claim 7 wherein:

the distal portion defines a distal length;

the bend defines an arc length; and a ratio of the distal length to the arc length is 0.8 or less.

9. The tube delivery system of claim 7 wherein an offset of a distal end of the elongate outer tube is 12.7 mm or more, the offset measured perpendicular to the proximal longitudinal axis of the proximal portion.

10. The tube delivery system of claim 1 further comprising:

a damper disposed within an interior volume of the hand piece, the damper comprising:

a stationary housing, the stationary housing defines an annular channel with a closed bottom and an open top, the annular channel disposed around a longitudinal central axis, and the annular channel has a depth from the closed bottom to the open top measured parallel to the longitudinal central axis;

a rotor defining a first arcuate vane and a second arcuate vane, the first and second arcuate vanes disposed in the annular channel; and a viscous fluid within the stationary housing and contacting the first and second arcuate vanes.

11. The tube delivery system of claim 10 wherein the viscous fluid is damping grease.

12. The tube delivery system of claim 10 further comprising:

a damping shaft defined by the rotor, the damping shaft protrudes from a first end of the damper, and the damping shaft coupled to the drive assembly; and a winding shaft defined by the rotor, the winding shaft protrudes opposite the damping shaft, and the winding shaft is operationally exposed through the stationary housing.

13. The tube delivery system of claim 1 wherein the introducer comprises polyetheretherketone (PEEK) having a wall thickness of 0.1016 mm or less, and an outside diameter of 2.032 mm or less.

* * * * *